US008980891B2

(12) United States Patent
Stirn et al.

(10) Patent No.: US 8,980,891 B2
(45) Date of Patent: Mar. 17, 2015

(54) CRYSTALLINE FORMS OF CERTAIN 3-PHENYL-PYRAZOLE DERIVATIVES AS MODULATORS OF THE 5-HT$_{2A}$ SEROTONIN RECEPTOR USEFUL FOR THE TREATMENT OF DISORDERS RELATED THERETO

(75) Inventors: Scott Stirn, San Diego, CA (US); Edward A. Lally, La Jolla, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 199 days.

(21) Appl. No.: 13/516,646

(22) PCT Filed: Dec. 16, 2010

(86) PCT No.: PCT/US2010/060848
§ 371 (c)(1),
(2), (4) Date: Jun. 15, 2012

(87) PCT Pub. No.: WO2011/075596
PCT Pub. Date: Jun. 23, 2011

(65) Prior Publication Data
US 2012/0252813 A1 Oct. 4, 2012

Related U.S. Application Data

(60) Provisional application No. 61/288,130, filed on Dec. 18, 2009.

(51) Int. Cl.
*A61K 31/5377* (2006.01)
*C07D 413/12* (2006.01)
*C07D 231/12* (2006.01)

(52) U.S. Cl.
CPC ................... *C07D 231/12* (2013.01)
USPC ....................................... 514/236.5; 544/140

(58) Field of Classification Search
CPC ............... A61K 31/5377; C07D 413/12
USPC ...................................... 544/140; 514/236.5
See application file for complete search history.

(56) References Cited

U.S. PATENT DOCUMENTS

| | | | |
|---|---|---|---|
| 4,099,012 A | 7/1978 | Gschwend |
| 4,405,644 A | 9/1983 | Kabbe et al. |
| 4,409,231 A | 10/1983 | Stenzel et al. |
| 4,985,352 A | 1/1991 | Julius et al. |
| 5,077,409 A | 12/1991 | Wissner |
| 5,128,351 A | 7/1992 | Wissner |
| 5,523,280 A | 6/1996 | Chene et al. |
| 5,661,024 A | 8/1997 | Kao et al. |
| 5,712,279 A | 1/1998 | Biller et al. |
| 5,739,135 A | 4/1998 | Biller et al. |
| 5,760,246 A | 6/1998 | Biller et al. |
| 5,886,044 A | 3/1999 | Widdowson et al. |
| 5,905,080 A | 5/1999 | Duckworth et al. |
| 5,945,382 A | 8/1999 | Cantegril et al. |
| 5,990,133 A | 11/1999 | Gaster et al. |
| 6,005,008 A | 12/1999 | Widdowson et al. |
| 6,028,085 A | 2/2000 | Bromidge |
| 6,054,472 A | 4/2000 | Armistead et al. |
| 6,140,509 A | 10/2000 | Behan et al. |
| 6,271,261 B1 | 8/2001 | Widdowson |
| 6,297,261 B1 | 10/2001 | Christophersen et al. |
| 6,417,393 B1 | 7/2002 | Christophersen et al. |
| 6,479,480 B1 | 11/2002 | Moyes et al. |
| 6,479,519 B1 | 11/2002 | Astles et al. |
| 6,531,291 B1 | 3/2003 | Kabbash et al. |
| 6,541,209 B1 | 4/2003 | Behan et al. |
| 6,696,475 B2 | 2/2004 | Dahl et al. |
| 6,706,749 B2 | 3/2004 | Dahl et al. |
| 6,784,183 B2 | 8/2004 | Lavielle et al. |
| 7,884,101 B2 | 2/2011 | Teegarden et al. |
| 7,960,413 B2 | 6/2011 | Schadt et al. |
| 2002/0025965 A1 | 2/2002 | Lavielle et al. |
| 2004/0102636 A1 | 5/2004 | Miller et al. |
| 2005/0054691 A1 | 3/2005 | Potter et al. |
| 2005/0080124 A1 | 4/2005 | Teegarden et al. |
| 2005/0267097 A1 | 12/2005 | Pinto et al. |
| 2006/0014705 A1 | 1/2006 | Howitz et al. |
| 2006/0063754 A1 | 3/2006 | Edgar et al. |
| 2006/0205792 A1 | 9/2006 | Wong et al. |
| 2006/0229335 A1 | 10/2006 | Teegarden et al. |
| 2007/0037827 A1 | 2/2007 | Nunes et al. |
| 2007/0072857 A1 | 3/2007 | Teegarden et al. |
| 2007/0207994 A1 | 9/2007 | Teegarden et al. |
| 2007/0244086 A1 | 10/2007 | Teegarden et al. |

(Continued)

FOREIGN PATENT DOCUMENTS

| | | |
|---|---|---|
| EP | 1 108 720 A1 | 6/2001 |
| EP | 1 558 582 B1 | 8/2005 |

(Continued)

OTHER PUBLICATIONS

Adams et al., "APD791, a Novel 5-HT2A Receptor Antagonist: Pharmacological Profile, Pharmacokinetics, Platelet and Vascular Biology," JPET # 153189, published on Jul. 23, 2009, 38 pages.

Andrzejewska-Buczko et al., "Serotonin in diabetic retinopathy," Klinika Oczna, 98(2):101-4 (1996) Abstract.

Antinori et al, "Diagnosis of AIDS-related focal brain lesions: a decision-making analysis based on clinical and neuroradiologic characteristics combined with polymerase chain reaction assays in CSF," Neurology, 48:687-694 (1997).

Berge, S. et al., "Pharmaceutical salts," Journal of Pharmaceutical Sciences, 66(1):1-19 (1977).

Berger et al., "Progressive multifocal leukoencephalopathy," Seminars in Neurology, 19:193-200 (1999).

Blier et al., "Putative mechanisms of action of antidepressant drugs in affective and anxiety disorders and pain," Journal of Psychiatry and Neuroscience, 26(1):37-43 (2000).

(Continued)

*Primary Examiner* — Rebecca Anderson

(57) ABSTRACT

Provided are certain solvates of 3-methoxy-N-[3-(2-methyl-2H-pyrazol-3-yl)-4-(2-morpholin-4-yl-ethoxy)-phenyl]-benzamide or a pharmaceutically acceptable salt thereof. Also provided are pharmaceutical compositions comprising such solvates and methods for their use.

13 Claims, 4 Drawing Sheets

(56) References Cited

U.S. PATENT DOCUMENTS

| | | |
|---|---|---|
| 2008/0015223 A1 | 1/2008 | Strah-Pleynet et al. |
| 2008/0200530 A1 | 8/2008 | Unett et al. |
| 2009/0186895 A1 | 7/2009 | Teegarden et al. |
| 2009/0189935 A1 | 7/2009 | Kunimatsu |
| 2009/0197935 A1 | 8/2009 | Teegarden et al. |

FOREIGN PATENT DOCUMENTS

| | | |
|---|---|---|
| EP | 1 734 039 A1 | 12/2006 |
| WO | WO-96/02138 A1 | 2/1996 |
| WO | WO-96/10559 A1 | 4/1996 |
| WO | WO-97/03967 A1 | 2/1997 |
| WO | WO-97/45111 A1 | 12/1997 |
| WO | WO-98/24785 A1 | 6/1998 |
| WO | WO-99/06354 A1 | 2/1999 |
| WO | WO-99/32436 A1 | 7/1999 |
| WO | WO-99/32463 A1 | 7/1999 |
| WO | WO-99/52927 A1 | 10/1999 |
| WO | WO-00/57877 A1 | 10/2000 |
| WO | WO-00/64866 A1 | 11/2000 |
| WO | WO-01/21160 A2 | 3/2001 |
| WO | WO 01/29008 A1 | 4/2001 |
| WO | WO-02/39987 A2 | 5/2002 |
| WO | WO-02/051833 A1 | 7/2002 |
| WO | WO-02/076464 A1 | 10/2002 |
| WO | WO-03/062206 A2 | 7/2003 |
| WO | WO-2004/028450 A2 | 4/2004 |
| WO | WO-2004/045118 A2 | 5/2004 |
| WO | WO-2004/058722 A1 | 7/2004 |
| WO | WO-2004/071426 A2 | 8/2004 |
| WO | WO-2004/085433 A2 | 10/2004 |
| WO | WO-2004/096771 A1 | 11/2004 |
| WO | WO-2005/012254 A1 | 2/2005 |
| WO | WO-2005/077345 A1 | 8/2005 |
| WO | WO-2005/103011 A1 | 11/2005 |
| WO | WO-2006/018662 A2 | 2/2006 |
| WO | WO-2006/049734 A2 | 5/2006 |
| WO | WO-2006/049941 A2 | 5/2006 |
| WO | WO-2006/055734 A2 | 5/2006 |
| WO | WO-2006/059149 A1 | 6/2006 |
| WO | WO-2006/060654 A2 | 6/2006 |
| WO | WO-2006/070394 A1 | 7/2006 |
| WO | WO-2006/076592 A1 | 7/2006 |
| WO | WO-2006/078610 A1 | 7/2006 |
| WO | WO-2006/079637 A1 | 8/2006 |
| WO | WO-2006/081335 A2 | 8/2006 |
| WO | WO-2006/086705 A1 | 8/2006 |
| WO | WO-2006/089871 A2 | 8/2006 |
| WO | WO-2006/095205 A1 | 9/2006 |
| WO | WO-2006/097766 A1 | 9/2006 |
| WO | WO-2006/100519 A1 | 9/2006 |
| WO | WO 2006/112464 A1 | 10/2006 |
| WO | WO-2006/116614 A1 | 11/2006 |
| WO | WO-2007/002559 A1 | 1/2007 |
| WO | WO-2007/026959 A2 | 3/2007 |
| WO | WO-2007/120600 A2 | 10/2007 |
| WO | WO-2007/129111 A1 | 11/2007 |
| WO | WO-2007/136680 A2 | 11/2007 |
| WO | WO-2007/136689 A2 | 11/2007 |
| WO | WO-2007/136703 A1 | 11/2007 |
| WO | WO-2007/136875 A2 | 11/2007 |
| WO | WO-2008/027483 A1 | 3/2008 |
| WO | WO-2008/042388 A1 | 4/2008 |
| WO | WO-2008/054748 A2 | 5/2008 |
| WO | WO-2009/023253 A2 | 2/2009 |
| WO | WO-2011/075596 A1 | 6/2011 |

OTHER PUBLICATIONS

Burger, A. "Isosterism and bioisosterism in drug design," Prog. Drug Res., 37: 287-371 (1991).

Cameron, N. et al., "The effects of 5-hydroxytryptamine 5-HT2 receptor antagonists on nerve conduction velocity and endoneurial perfusion in diabetic rats," Naunyn Schmiedeberg's Archive of Pharmacology, 367:607-14 (2003).

Casey, C. et al., "Constitutively active mutant 5HT2A serotonin receptors: inverse agonist activity of classical 5HT2A antagonists," Society for Neuroscience, 22:1778 (1996) Abstract.

Catalán et al., "New Ultraviolet Stabilizers: 3- and 5-(2'-Hydroxyphenyl)pyrazoles," J. Am. Chem. Soc., 114, 5039-5048 (1992).

Cazzola, M. et al., "5-HT modifiers as a potential treatment of asthma," TiPS, 21:13-6 (2000).

Chang, C. et al. "Ipsapirone and ketanserin protects against circulatory shock, intracranial hypertension, and cerebral ischemia during heatstroke," Shock 24(4): 336-340 (2005).

Chang, F. A. et al., "Mechanism of ocular hypotensive action of ketanserin," Journal of Ocular PharmaCology, 1(2):137-47 (1985).

Cohen-Mansfield, J. et al., "Agitated behaviors in the elderly I. a conceptual review," JAGS, 34(10):711-21 (1986).

De Bie et al., "Modulation of airway hyperresponsiveness and eosinophilia by selective histamine and 5-HT receptor antagonists in a mouse model of allergic asthma," British Journal of Pharmacology, 124:857-64 (1998).

Deuchar, G. et al. "The role of 5-hydroxytryptamine in the control of pulmonary vascular tone in a rabbit model of pulmonary hypertension secondary to left ventricular dysfunction," Pulm. Pharmacol. Ther. 18(1):23-31(2005).

Dosa et al., "Synthesis and SAR of solubilized pyrazole derivatives as 5-HT2A inverse-agonists for platelet aggregation," 232nd ACS National Meeting, Medi 431 (2006).

Elliott et al., "4-Oxospiro[benzopyran-2,4'-[piperidines] as Class III Antiarrhythmic Agents. Pharmacological Studies on 3,4-Dihydro-1'-[2-(benzofurazan-5-yl)-ethyl]-6methanesulfonamidospirol[(2H)-1-benzopyran-2,4'-piperidin]-4-one (L-691,131)", J. Med. Chem., 35:3973-3976 (1992).

Elphick et al., "The human polyomavirus, JCV, uses serotonin to infect cells," Science, 306:1380-3 (2004).

Fujita et al., "Sarpogrelate treatment reduces restenosis after coronary stenting," Am Heart Journal, 145:16 (2003).

Fujiwara et al., "Augmented responses to 5-HT2-receptor-mediated vasoconstrictions in atherosclerotic rabbit common carotid arteries," Journal of Cardiovascular Pharmacology, 26:503-510, 1995.

Greene et al., Protecting Groups in Organic Synthesis, 3rd Edition, 1999 (Wiley).

Gründer, G. et al., "Time course of 5-HT2A receptor occupancy in the human brain after a single dose of the putative antipsychotic drug MDL 100,907 measured by positron emission tomography," Neuropsychopharmacology, 17(3):175-85 (1997).

Hayashi, T. et al. "Sarpogrelate HCl, a selective 5-HT2A antagonist, retards the progression of atherosclerosis through a novel mechanism," Atherosclerosis 168: 23-31 (2003).

Herrick-Davis et al., "Activating mutations of the serotonin 5HT2c receptor," Journal of Neurochemistry, 69(3):1138-44 (1997).

Herrick-Davis, K. et al., "Constitutively active 5HT2C serotonin receptor created by site directed mutagenesis," Society for Neuroscience, 22:1779 (1996) Abstract.

Higuchi et al., "Pro-Drugs and Novel Delivery Systems," vol. 14 of the ACS Symposium Series; and in Bioreversible Carriers in Drug Design, ed. Edward B. Roche, American Pharmaceutical Association and Pergamon Press, 1987.

Horibe, E., "Sarpogrelate, a 5-HT2 receptor blocker, may have a preconditioning-like effect in patients with coronary artery disease," Circulation Research 68:68-72, 15 (2004).

Kanayama, M. et al., "New treatment of lumbar disc herniation using 5-hydroxytryptamine2A receptor inhibitor: a randomized controlled trial," Journal of Neurosurgery: Spine, 2:441-6 (2005).

Katz et al., "Comparison of risperidone and placebo for psychosis and behavioral disturbances associated with dementia: a randomized double-blind trial," Journal of Clinical Psychiatry, 60(2): 107-15 (1999).

Kitagawa et al., "Beckman Rearrangement of O-4 Pentenyl Oxime through N-Bromosuccinimide-Mediated Activating Process," Chem. Pharm. Bull., 45(1) 32-35 (1997).

Koss et al., "Assessing patterns of agitation in Alzheimer's disease patients with the Cohen-Mansfield agitation inventory," Alzheimer's Disease and Associated Disorders, 11(S2):545-550 (1997).

(56) References Cited

OTHER PUBLICATIONS

Krieger et al., "Novel immunosuppressants," Pediatr Transplantation, 8:594-599 (2004).
Landolt, H. et al., "Serotonin-2 receptors and human sleep: effect of a selective antagonist on EEG power spectra," Neuropsychopharmacology, 21(3):455-66 (1999).
Le Bas et al., "Radioiodinated analogs of EP 00652218 for the exploration of the tachykinin NK1 receptor by spect," Journal of Labelled Cpd. Radiopharm., 44(S1):S280-2 (2001).
Major et al., "Establishment of a line of human fetal glial cells that supports JC virus multiplication," PNAS USA, , 82:1257-1261 (1985).
Marcos et al., "Serotonin-induced smooth muscle hyperplasia in various forms of human pulmonary hypertension," Circ. Res. 94(9): 1263-70 (2004).
Mastropasqua, L. et al., "Ocular hypertensive effect of ketanserin in patients with primary open angle glaucoma," Acta Ophthalmologica Scandinavica, 75:24-5 (1997).
Miao et al., "Ketanserin stabilizes blood pressure in conscious spontaneously hypertensive rats," Clin. Exp. Pharmacol. Physio. 30(3):189-193, (2003).
Mueller, "Drug immunosuppression therapy for adult heart transplantation. Part 1: immune response to allograft and mechanism of action of immunosuppressants," Ann Thorac Surg. 77:354-362 (2004).
Muto, T. et al., "Protective effects of sarpogrelate, a 5HT2A antagonist, against postischemic myocardial dysfunction in guinea-pig hearts," Molecular and Cellular Biochemistry, 272:119-32 (2005).
National Institutes of Health, "Facts about Insomnia," NIH publication No. 95/3801 (1995).
Nishiyama, T., "Effects of 5HT2A receptor antagonist, sarpogrelate on thermal or inflammatory pain," European Journal of Pharmacology, 516:18-22 (2005).
Nomura, S. et al., "5HT2A receptor antagonist increases circulating adiponectin in patients with type 2 diabetes," Blood Coagulation and Fibrinolysis, 16(6):423-8 (2005).
Pawlak D. et al., "A potent 5-hydroxytryptamine receptor (5-HT2A) antagonist, DV-7028, delays arterial thrombosis development in rats," Thrombosis Research 90: 259-270 (1998).
Pietraszek, M. H. et al., "Blood serotonergic mechanisms in type 2 (non-insulin dependant) diabetes mellitus," Thrombosis Research, 66:765-74 (1992).
Portegies et al., "Guidelines for the diagnosis and management of neurological complications of HIV infection," Eur. J. Neurol. 11:297-304 (2004).
Querbes et al., "A JC virus-induced signal is required for infection of glial cells by a clathrin- and eps15-dependent pathway," J Virology, 78:250-256 (2004).
Satomura et al., "Sarpogrelate, a specific 5HT2-receptor antagonist, improves the coronary microcirculation in coronary artery disease," Clinical Cardiology, 25:28-32 (2002).
Sawnyok et al., "Antidepressants as analgesics: an overview of central and peripheral mechanisms of action," Journal of Psychiatry and Neuroscience, 26(1):21-9 (2001).
Sharpley, A.L. et al., "Slow wave sleep in humans: role of 5HT2A and 5HT2c receptors," Neuropharmacology, 33(3/4):467-71 (1994).
Shibata et al., "Adiponectin protects against myocardial ischemiareperfusion injury through AMPK- and COX-2- dependent mechanisms," Nature Medicine, advanced online Publication:1-8, (2005).
Silva, A., Chronic treatment with mianserin prevents DOCA-salt hypertension in rats—evidence for the involvement of central 5-HT2 receptors,' Eur J. Pharmacol. 518(2-3): 152-172 (2005).
Singh et al., "Immunosuppressive-associated leukoencephalopathy in organ transplant recipients," Transplantation, 69:467-472 (2000).
Smith et al., "Test-retest variability of serotonin 5HT2A receptor binding measured with positron emission tomography and [18 F]altanserin in the human brain," Synapse, 30:380-92 (1998).
Staley, J. et al., "Comparison of [18 F]altanserin and [18 F]deuteroaltanserin for PET imaging of serotonin2A receptors in baboon brain: pharmacological studies," Nuclear Medicine and Biology, 28:271-9 (2001).
Stenzel et al., Document No. 94:208858, 1981, retrieved from CAPLUS.
Strah-Pleynet et al., "Discovery and SAR of novel 5HT2A inverse-agonists," 27th ACS National Meeting, MEDI 270 (2004).
Street, J. et al., "Olanzapine treatment of psychotic and behavioral symptoms in patients with Alzheimer's disease in nursing care facilities," Archive of General Psychiatry, 57:968-76 (2000).
Takahashi, T. et al., "Sarpogrelate hydrochloride, a serotonin 2A receptor antagonist, reduces in patients with early-stage diabetic nephropathy," Diabetes Research and Clinical 58:123-9 (2002).
Takenaka et al., "The effect of Anplag® (sarpogrelate HCL). Novel selective 5-HT2 antagonist of intraocular pressure in glaucoma patients," Investigative Ophthalmology & Visual Science, 36(4):S734 (1995) Abstract.
Talvik-Lofti, M. et al., "High HT2A occupancy in M100907-treated schizophrenic patients," Psychopharmacology, 148:400-3 (2000).
The International Classification of Sleep Disorders, Revised Diagnostic and Coding Manual, American Academy of Sleep Medicine (2001) pp. 1-336 (also includes table of contents and glossary).
Topliss, J.G., "A Manual Method for Applying the Hansch Approach to Drug Design," J. Med. Chem. 20(4), pp. 463-469. (1977).
Turpin, "The next generation of HIV/AIDS drugs: novel and developmental antiHIV drugs and targets," Expert Rev Anti Infect Ther. Jun;1(1):97-128 (2003).
U.S. Appl. No. 11/597,306, Restriction Requirement dated Apr. 7, 2008.
U.S. Appl. No. 11/602,164, Advisory Action dated Sep. 9, 2009.
U.S. Appl. No. 11/602,164, Notice of Allowance dated Sep. 27, 2010.
U.S. Appl. No. 11/602,164, Office Action dated Jan. 2, 2009.
U.S. Appl. No. 11/602,164, Office Action dated Jul. 23, 2008.
U.S. Appl. No. 11/602,164, Office Action dated Jun. 19, 2009.
U.S. Appl. No. 11/602,164, Restriction Requirement dated Jan. 24, 2008.
U.S. Appl. No. 12/301,172, Notice of Allowance dated Nov. 22, 2011.
U.S. Appl. No. 12/301,172, Office Action dated Jul. 27, 2011.
U.S. Appl. No. 12/301,172, Restriction Requirement dated Feb. 14, 2011.
U.S. Appl. No. 12/301,180 Notice of Allowance dated Nov. 28, 2011.
U.S. Appl. No. 12/301,180, Office Action dated Jul. 27, 2011.
U.S. Appl. No. 12/301,180, Office Action dated Oct. 26, 2011.
U.S. Appl. No. 12/301,180, Restriction Requirement dated Feb. 14, 2011.
U.S. Appl. No. 12/301,180. Notice of Allowance dated Nov. 28, 2011.
U.S. Appl. No. 12/301,212, Office Action dated Apr. 2, 2012.
U.S. Appl. No. 12/301,212, Restriction Requirement dated Oct. 14, 2011.
U.S. Appl. No. 12/976,887, Office Action dated Feb. 15, 2012.
U.S. Appl. No. 12/976,887, Office Action dated Sep. 7, 2011.
U.S. Appl. No. 12/976,887, Restriction Requirement dated Mar. 14, 2011.
Vacante et al., "Extension of JC virus host range to monkey cells by insertion of a simian virus 40 enhancer into the JC virus regulatory region," Virology, 170:353-361, (1989).
Verstraete, M. "Prevention of atherosclerotic complications: controlled trial of ketanserin," British Medical Journal, 298:424-30 (1989).
Vikenes et al., "Serotonin is associated with coronary artery disease and cardiac events," Circulation, 100:483-9 (1999).
Vippagunta, et al. "Crystalline solids," Advanced Drug Delivery Reviews 48:3-26 (2001).
Wilson, H et al., "LY53857, a HT2 receptor antagonist delays occlusion and inhibits platelet aggression in a rabbit model of carotid artery occlusion," Thrombosis and Haemostasis, 66 (3) 355-60 (1991).

(56) References Cited

OTHER PUBLICATIONS

Winokur, A. et al., "Acute effects of Mirtazapine on sleep continuity and sleep architecture in depressed patients: a pilot study," Biological Psychiatry, 48:75-8 (2000).

Yamada et al., "Phase I/II trial of didanosine (2',3'-dideoxyinosine) in hemophiliac patients with AIDS or AIDS-related complex," Clin. Diag. Virol. 1:245-256 (1993).

Nitanda et al., "Contribution of the peripheral 5-HT$_{2A}$ receptor to mechanical hyperalgesia in a rat model of neuropathic pain," Neurochemistry International 47, pp. 394-400 (2005).

Yamashita et al., "Conjunctive effects of the 5HT(2) receptor antagonist, sarpogrelate, on thrombolysis with modified tissue plasminogen activator in different laser-induced thrombosis models." Haemostasis, 30:321-332, (2000).

Collier et al., "Radiosynthesis and in vivo evaluation of the psuedopeptide .delta.-opioidantagonist C25 1]—ITIPP(.PSI.)," Journal of Labelled Cpd. Radiopharm., 42 (Suppl. 1 ):S264-6 (1999).

Hong et al., "Topical ketanserin attenuates hyeralgesia and inflammation in arthritis in rats," Pain 124, pp. 27-33 (2006).

Nakajima et al., The nociceptive mechanism of 5-hydroxtryptamine released into the peripheral tissue in acute inflammatory pain in rats, European Journal of Pain 13, pp. 441-447 (2009).

Nitanda et al., "Contribution of the peripheral 5-HTzA receptor to mechanical hyperalgesia in a ratmodel of neuropathic pain," Neurochemistry International 4 7, pp. 394-400 (2005).

Yamashita et al., "Conjunctive effects of the 5HT(2) receptor antagonist, sarpogrelate, onthrombolysis with modified tissue plasminogen activator in different laser-induced thrombosis models,"Haemostasis, 30:321-332, (2000).

Zhu et al., "Synthesis and mode of action of 125 1- and 3 H-labeled thieno[2,3,-c]pyridine antagonistsof cell adhesion molecule expression," Journal of Organic Chemistry, 67:943-8 (2002).

… (1)

CRYSTALLINE FORMS OF CERTAIN 3-PHENYL-PYRAZOLE DERIVATIVES AS MODULATORS OF THE 5-HT$_{2A}$ SEROTONIN RECEPTOR USEFUL FOR THE TREATMENT OF DISORDERS RELATED THERETO

This application is a 35 USC 371 National Stage Entry of PCT/US2010/060848 filed Dec. 16, 2010, and claims priority to U.S. Provisional Application No. 61/288,130 filed Dec. 18, 2009, which are incorporated herein by reference.

Receptors for serotonin (5-hydroxytryptamine, 5-HT) are an important class of G protein coupled receptors. Serotonin receptors are divided into seven subfamilies, referred to as 5-HT$_1$ through 5-HT$_7$, inclusive. These subfamilies are further divided into subtypes. For example, the 5-HT$_2$ subfamily is divided into three receptor subtypes: 5-HT$_{2A}$, 5-HT$_{2B}$, and 5-HT$_{2C}$. Certain phenyl-pyrazoles are modulators of 5-HT$_{2A}$ serotonin receptor activity useful in the treatment of platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders, progressive multifocal leukoencephalopathy, and the like.

Provided is 3-methoxy-N-[3-(2-methyl-2H-pyrazol-3-yl)-4-(2-morpholin-4-yl-ethoxy)-phenyl]-benzamide hydrate.

Also provided is (4-(2-(4-(3-methoxybenzamido)-2-(1-methyl-1H-pyrazol-5-yl)phenoxy)ethyl)morpholin-4-ium carboxyformate ethanol solvate.

Also provided are pharmaceutical compositions comprising one or more pharmaceutically acceptable diluents and a therapeutically effective amount of at least one solvate described herein.

Also provided are processes for preparing the solvates described herein as well as solvates prepared by the processes.

Also provided are pharmaceutical compositions prepared by formulating a therapeutically effective amount of at least one solvate described herein with one or more pharmaceutically acceptable carrier to provide the pharmaceutical composition.

Also provided are methods for modulating the activity of a 5-HT$_{2A}$ serotonin receptor in an individual by administering a pharmaceutical compositions prepared by formulating a therapeutically effective amount of at least one solvate described herein with one or more pharmaceutically acceptable carrier to provide the pharmaceutical composition.

Also provided are methods for treating a 5-HT$_{2A}$ mediated disorder in an individual by administering a pharmaceutical compositions prepared by formulating a therapeutically effective amount of at least one solvate described herein with one or more pharmaceutically acceptable carrier to provide the pharmaceutical composition.

Figure 1:
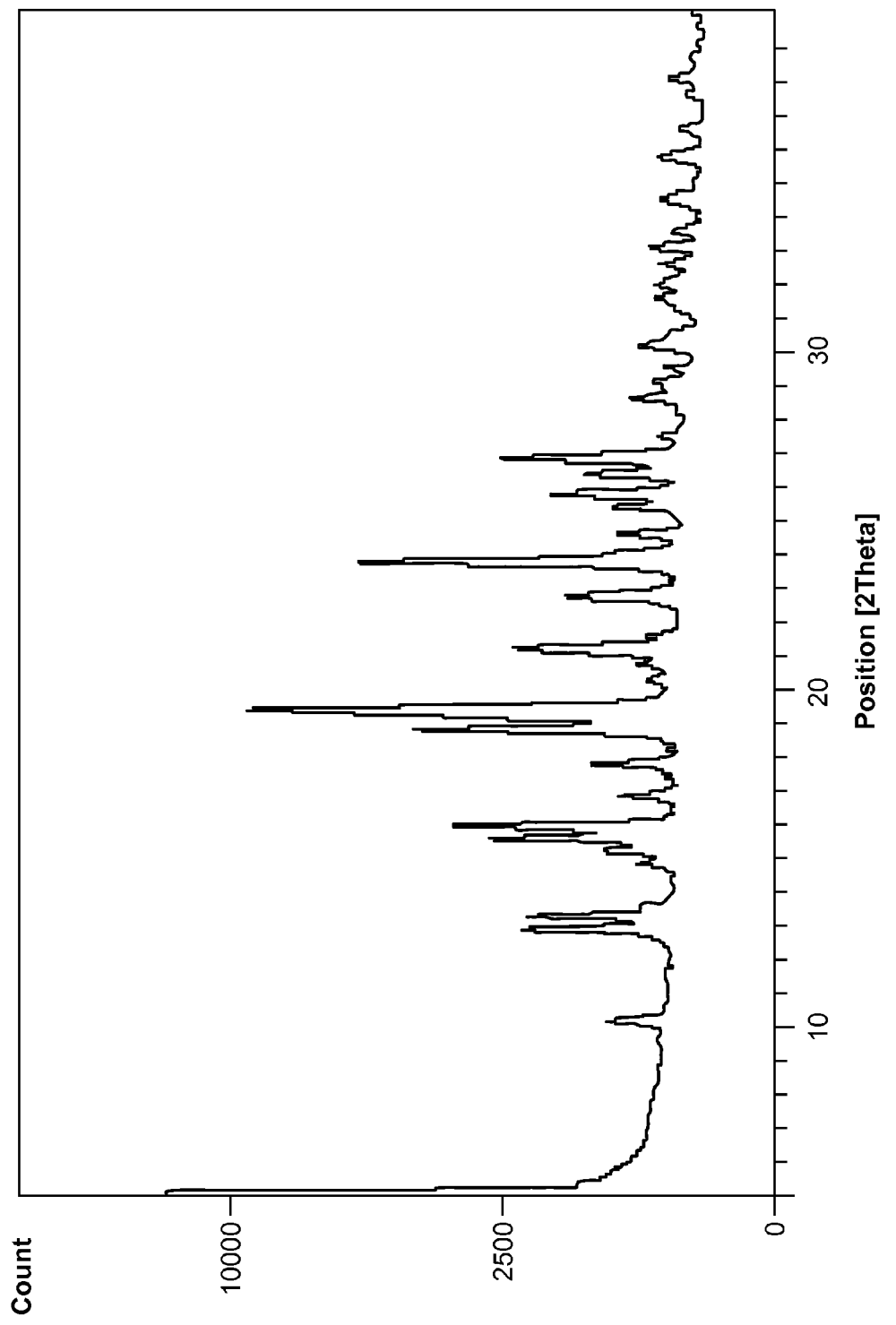
FIG. 1 shows powder X-ray diffraction pattern of 3-methoxy-N-[3-(2-methyl-2H-pyrazol-3-yl)-4-(2-morpholin-4-yl-ethoxy)-phenyl]-benzamide hydrate.

For clarity and consistency, the following definitions will be used throughout this document.

"Polymorphism" is defined as in the International Conference on Harmonization (ICH) Guideline Q6A Guideline: Specifications for New Drug Substances and Products: Chemical Substances, October 1999 and refers to the occurrence of different solid forms of the same drug substance. Polymorphs can be unsolvated or solvated, such as hydrated, crystal forms. Unsolvated crystal forms are crystals that do not have solvent incorporated within the crystal structure and include anhydrous crystal forms or anhydrates. Solvated crystal forms, or solvates, are crystalline solid adducts containing either stoichiometric or nonstoichiometric amounts of solvent molecules incorporated within the crystal structure. If the incorporated solvent is water, the solvates are also commonly known as hydrates. Amorphous solids consist of disordered arrangements of molecules and do not possess a distinguishable crystal lattice.

"Pharmaceutically acceptable salt" refers to a pharmaceutically acceptable organic or inorganic acid or base salt. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

In addition, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The term "3-methoxy-N-[3-(2-methyl-2H-pyrazol-3-yl)-4-(2-morpholin-4-yl-ethoxy)-phenyl]-benzamide" refers to a chemical entity with the following structure:

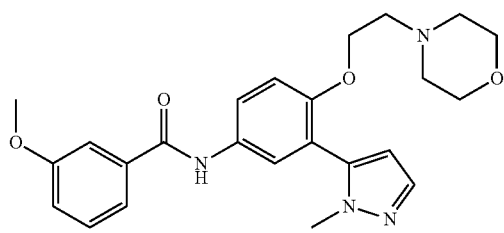 [SMILES: COc1cccc(C(=O)Nc2ccc(OCCN3CCOCC3)c(-c3ccnn3C)c2)c1]

As used herein, the term "treating" refers to, for example, preventing, inhibiting, as well as ameliorating a disease, condition or disorder in an individual.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting further development of the pathology and/or symptomatology) such as stabilizing viral load in the case of a viral infection; and (3) ameliorating the disease; for example, ameliorating a disease, condition or disorder in an individual that is experiencing or displaying the pathology or symptomatology of the disease, condition or disorder (i.e., reversing the pathology and/or symptomatology) such as lowering viral load in the case of a viral infection.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to hydrates, as well as all combinations of uses and medical indications described herein, are specifically embraced by the present invention just as if each and every combination was individually explicitly recited. In addition, all subcombinations of the hydrates listed in the embodiments are also specifically embraced by the present invention just as if each and every subcombination of hydrates and subcombination of uses and medical indications was individually and explicitly recited herein.

Provided is 3-methoxy-N-[3-(2-methyl-2H-pyrazol-3-yl)-4-(2-morpholin-4-yl-ethoxy)-phenyl]-benzamide hydrate. In some embodiments, the 3-methoxy-N-[3-(2-methyl-2H-pyrazol-3-yl)-4-(2-morpholin-4-yl-ethoxy)-phenyl]-benzamide hydrate contains water ranging from about 3.5% to about 4.2%, such as about 3.8%, by weight, as measured by TGA.

Provided is (4-(2-(4-(3-methoxybenzamido)-2-(1-methyl-1H-pyrazol-5-yl)phenoxy)ethyl)morpholin-4-ium carboxyformate ethanol solvate. In some embodiments, the (4-(2-(4-(3-methoxybenzamido)-2-(1-methyl-1H-pyrazol-5-yl)phenoxy)ethyl)morpholin-4-ium carboxyformate ethanol solvate contains ethanol ranging from about 5.0% to about 6.0%, such as about 5.3%, by weight, as measured by TGA.

The solvates described herein may be identified by one or more solid state analytical methods. For example, the solvates may be characterized according to one or more of, e.g., X-ray diffraction, unit cell constants, Fourier transform infrared spectroscopy, differential scanning calorimetry curve data, solid state nuclear magnetic resonance spectroscopy, and Raman spectroscopy.

A sample is considered to be a solvate if it is characterized as such by at least one of the methods described herein, regardless of any inconsistent or contradictory results obtained by any of the other methods described above. In addition, a sample is considered to be a solvate if it is characterized as such by at least one of the above methods under a particular set of experimental conditions, regardless of any inconsistent or contradictory results obtained by the same method under a different set of experimental conditions.

In some embodiments, the solvates described herein may be characterized according to differential scanning calorimetry curve data (DSC). For DSC, it is known that the temperatures observed will depend upon the rate of temperature change as well as sample preparation technique and the particular instrument employed. Thus, the values reported herein relating to DSC thermograms can vary by plus or minus about 4° C.

In some embodiments, the solvates may be characterized according to melting point. For example, also provided is 3-methoxy-N-[3-(2-methyl-2H-pyrazol-3-yl)-4-(2-morpholin-4-yl-ethoxy)-phenyl]-benzamide hydrate having a melting endotherm with an onset of about 105±4° C., as measured by differential scanning calorimetry.

Also provided is an embodiment of (4-(2-(4-(3-methoxybenzamido)-2-(1-methyl-1H-pyrazol-5-yl)phenoxy)ethyl)morpholin-4-ium carboxyformate ethanol solvate having a melting endotherm with an onset of about 170±4° C., as measured by differential scanning calorimetry.

Figure 2:
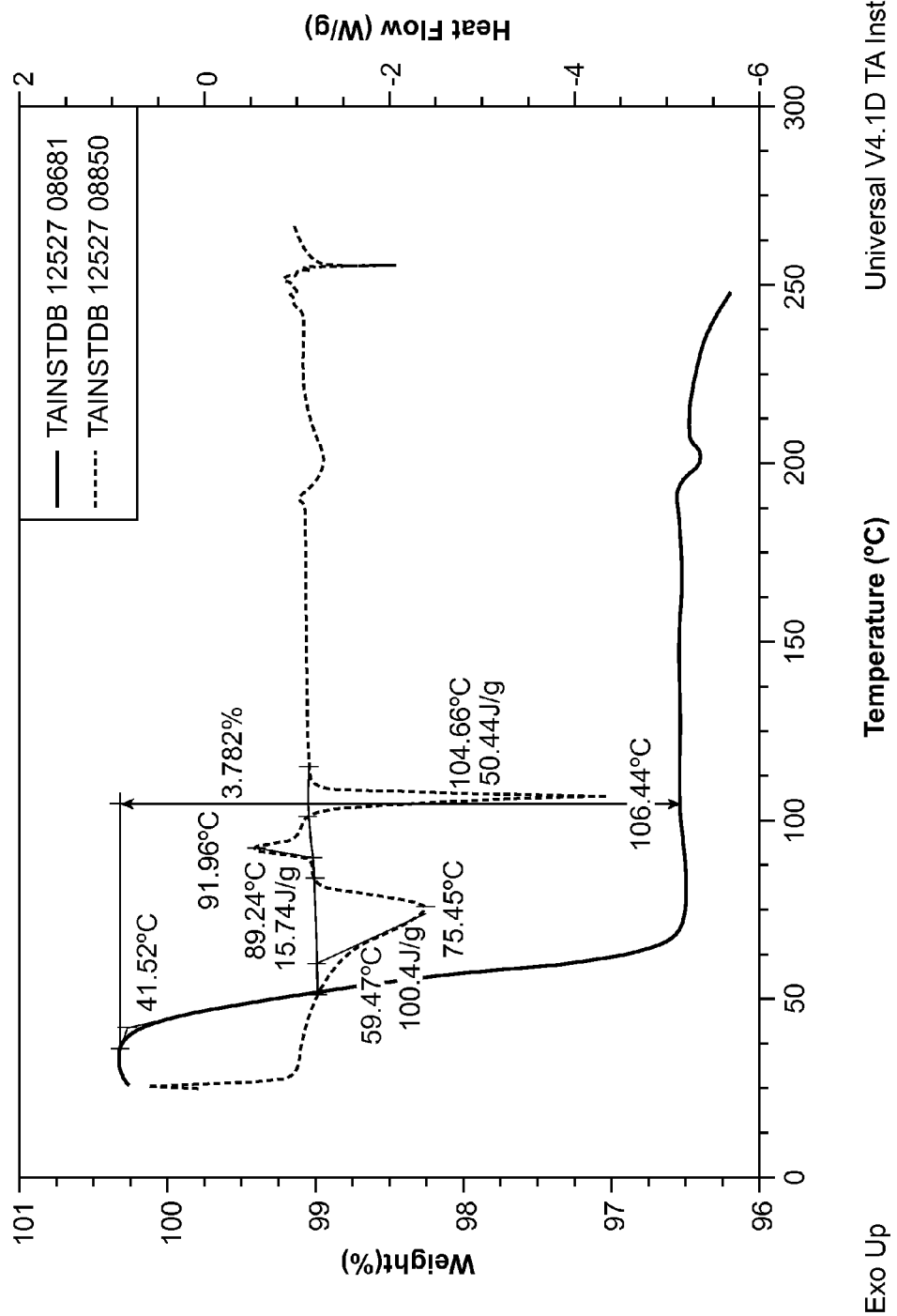
FIG. 2 shows differential scanning calorimetry (DSC) and thermogravimetric analyses (TGA) plots for 3-methoxy-N-[3-(2-methyl-2H-pyrazol-3-yl)-4-(2-morpholin-4-yl-ethoxy)-phenyl]-benzamide hydrate.

In some embodiments, the thermogravimetric analysis profile of the 3-methoxy-N-[3-(2-methyl-2H-pyrazol-3-yl)-4-(2-morpholin-4-yl-ethoxy)-phenyl]-benzamide hydrate is substantially as shown in FIG. 2 wherein by "substantially" is meant that the reported TGA features can vary by about ±5° C.

Figure 3:
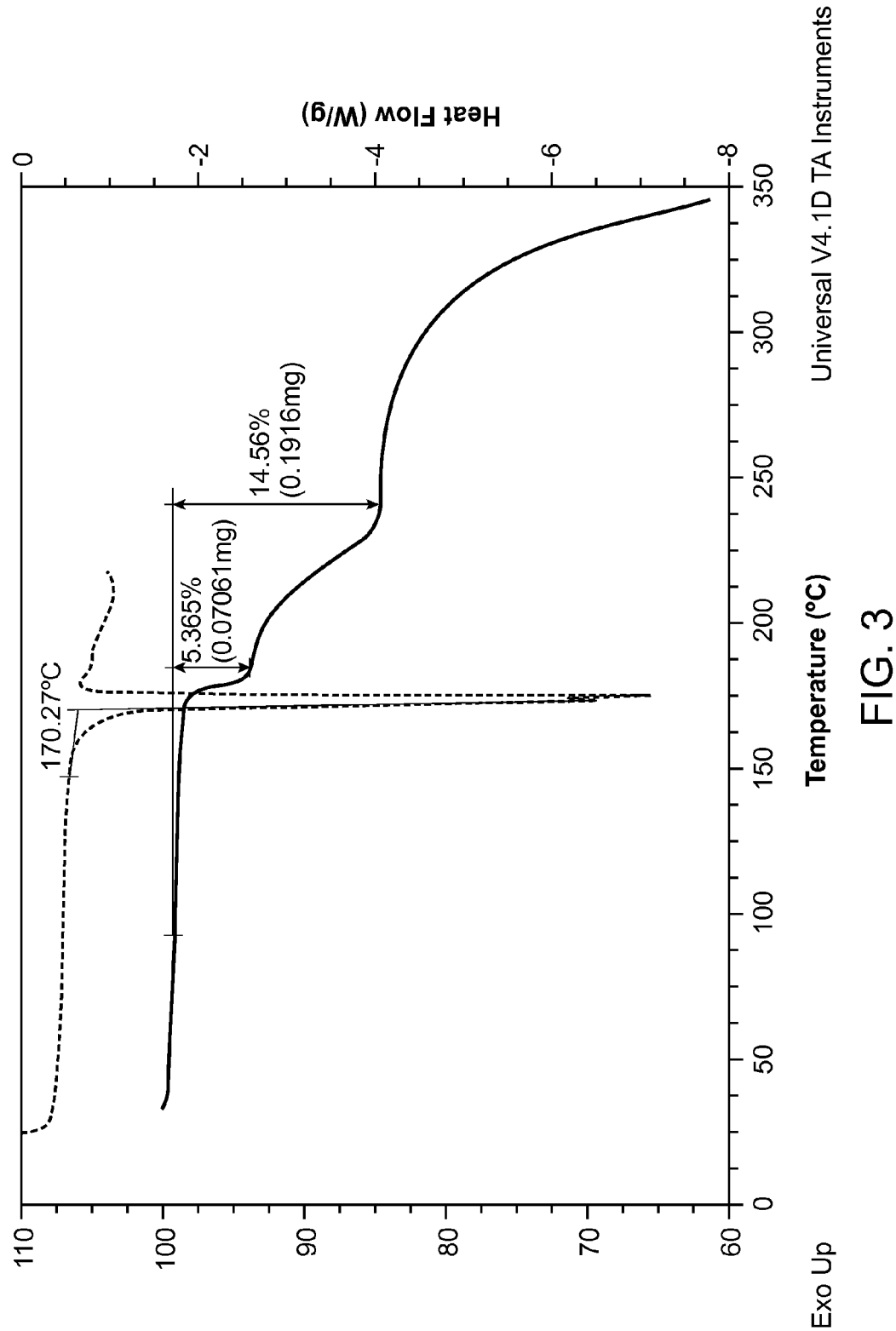
FIG. 3 shows representative DSC and TGA plots for (4-(2-(4-(3-methoxybenzamido)-2-(1-methyl-1H-pyrazol-5-yl)phenoxy)ethyl)morpholin-4-ium carboxyformate ethanol solvate.

In some embodiments, the thermogravimetric analysis profile of the (4-(2-(4-(3-methoxybenzamido)-2-(1-methyl-1H-pyrazol-5-yl)phenoxy)ethyl)morpholin-4-ium carboxyformate ethanol solvate is substantially as shown in FIG. 3 wherein by "substantially" is meant that the reported TGA features can vary by about ±5° C.

In some embodiments, the solvates described herein may be characterized according to X-ray powder diffraction. The intensity in the X-ray powder diffraction diagram of different batches of the solvates described herein may vary, because of preferred orientation or even variable hydration. Furthermore, in the X-ray powder diffraction diagram of the solvates described herein, there can be differences in the measured peaks, due to the difference of the measuring instruments and testing conditions during the X-ray diffraction measurement. But notwithstanding experimental and machine errors, and principles such as preferred orientation, one skilled in the art can find sufficient information in the XRPD data provided herein to identify a specific crystalline form. In other words, not all of the data are necessary to identify the crystalline form.

Owing to natural deviations in the samples or in the measuring method, the 2θ values of the peaks can be stated with an accuracy of +/−0.2000 degrees 2θ. However, it is common to see some measurement variations in reported data due to, for example, instrumental variations and environmental disturbances, such as preferred orientation, sample surface and inter-apparatus variability, and thus even the same forms of a compound may not exhibit the same exact XRPD data (in terms of D-spacing and peak intensity) all the time. Thus, even when the specific numerical values are not identical in every measurement, if the overall pattern is reproduced and the peak locations and relative peak intensities are sufficiently similar, one of skill in the art, using known and accepted techniques for such evaluation, can conclude that all of the obtained data demonstrate a single crystalline form.

For example, also provided is an embodiment of 3-methoxy-N-[3-(2-methyl-2H-pyrazol-3-yl)-4-(2-morpholin-4-yl-ethoxy)-phenyl]-benzamide hydrate with an XRPD, measured with CuKα radiation, having peaks chosen from those having about the following values: 5.0998, 18.7064, 19.1157, 19.3029, and 23.6567. Again, those multiple peaks are sufficient but not necessary to identify that specific crystalline embodiment.

Also provided is an embodiment of 3-methoxy-N-[3-(2-methyl-2H-pyrazol-3-yl)-4-(2-morpholin-4-yl-ethoxy)-phenyl]-benzamide hydrate with an XRPD, measured with CuKα radiation, having peaks chosen from those having about the following values: 5.0998, 12.7991, 15.4771, 15.8201, 18.7064, 19.1157, 19.3029, 21.1196, 23.6567, and 26.7255. Again, those multiple peaks are sufficient but not necessary to identify that specific crystalline embodiment.

Also provided is an embodiment of 3-methoxy-N-[3-(2-methyl-2H-pyrazol-3-yl)-4-(2-morpholin-4-yl-ethoxy)-phenyl]-benzamide hydrate with an XRPD, measured with CuKα radiation, having one or more peaks chosen from those set forth in Table 1 below. Again, those multiple peaks are sufficient but not necessary to identify that specific crystalline embodiment.

TABLE 1

| PXRD Peaks | | | | |
|---|---|---|---|---|
| Pos. [°2Th.] | Height [cts] | FWHM [°2Th.] | d-spacing [Å] | Rel. Int. [%] |
| 5.0998 | 16685.21 | 0.1338 | 17.32837 | 100.00 |
| 10.1034 | 502.62 | 0.1171 | 8.75519 | 3.01 |
| 12.7991 | 1743.46 | 0.1506 | 6.91662 | 10.45 |
| 13.2049 | 1636.11 | 0.1338 | 6.70497 | 9.81 |
| 13.4980 | 294.04 | 0.1004 | 6.56007 | 1.76 |
| 14.7576 | 235.93 | 0.1004 | 6.00284 | 1.41 |
| 15.0902 | 586.25 | 0.0836 | 5.87129 | 3.51 |
| 15.4771 | 2317.73 | 0.1338 | 5.72535 | 13.89 |
| 15.8201 | 3116.02 | 0.1673 | 5.60201 | 18.68 |
| 16.7468 | 417.97 | 0.1171 | 5.29402 | 2.51 |
| 17.6943 | 789.80 | 0.1338 | 5.01264 | 4.73 |
| 18.7064 | 3916.41 | 0.1506 | 4.74364 | 23.47 |
| 19.1157 | 4737.16 | 0.0669 | 4.64298 | 28.39 |
| 19.3029 | 8968.85 | 0.1506 | 4.59837 | 53.75 |
| 20.2058 | 232.91 | 0.1673 | 4.39490 | 1.40 |
| 20.6138 | 326.86 | 0.1171 | 4.30881 | 1.96 |
| 21.1196 | 1942.76 | 0.2676 | 4.20672 | 11.64 |
| 22.6440 | 1152.76 | 0.1506 | 3.92689 | 6.91 |
| 23.6567 | 5478.93 | 0.2007 | 3.76103 | 32.84 |
| 24.4655 | 505.78 | 0.1338 | 3.63850 | 3.03 |
| 25.2482 | 568.85 | 0.1171 | 3.52745 | 3.41 |
| 25.6649 | 1398.90 | 0.1840 | 3.47111 | 8.38 |
| 26.1913 | 838.97 | 0.1840 | 3.40253 | 5.03 |
| 26.7255 | 2159.11 | 0.1506 | 3.33573 | 12.94 |
| 27.3900 | 169.35 | 0.1338 | 3.25628 | 1.01 |
| 28.4861 | 412.85 | 0.1673 | 3.13344 | 2.47 |

TABLE 1-continued

| PXRD Peaks | | | | |
|---|---|---|---|---|
| Pos. [°2Th.] | Height [cts] | FWHM [°2Th.] | d-spacing [Å] | Rel. Int. [%] |
| 29.0404 | 243.67 | 0.1673 | 3.07488 | 1.46 |
| 29.4217 | 135.96 | 0.1338 | 3.03588 | 0.81 |
| 30.0303 | 374.65 | 0.2342 | 2.97573 | 2.25 |
| 30.4984 | 153.30 | 0.1004 | 2.93112 | 0.92 |
| 31.4985 | 232.22 | 0.2007 | 2.84030 | 1.39 |
| 31.8583 | 235.44 | 0.1338 | 2.80904 | 1.41 |
| 32.4897 | 198.24 | 0.1338 | 2.75588 | 1.19 |
| 32.9338 | 269.98 | 0.1171 | 2.71973 | 1.62 |
| 33.4436 | 128.77 | 0.1673 | 2.67942 | 0.77 |
| 34.3265 | 212.68 | 0.2342 | 2.61250 | 1.27 |
| 35.7053 | 208.51 | 0.2676 | 2.51472 | 1.25 |
| 36.5207 | 92.02 | 0.2007 | 2.46042 | 0.55 |
| 37.9565 | 182.89 | 0.2342 | 2.37059 | 1.10 |

In some embodiments, the 3-methoxy-N-[3-(2-methyl-2H-pyrazol-3-yl)-4-(2-morpholin-4-yl-ethoxy)-phenyl]-benzamide hydrate contains no more than about 50% of any other polymorphic forms. In some embodiments, the 3-methoxy-N-[3-(2-methyl-2H-pyrazol-3-yl)-4-(2-morpholin-4-yl-ethoxy)-phenyl]-benzamide hydrate contains no more than about 10% of any other polymorphic forms. In some embodiments, the 3-methoxy-N-[3-(2-methyl-2H-pyrazol-3-yl)-4-(2-morpholin-4-yl-ethoxy)-phenyl]-benzamide hydrate contains no more than about 5% of any other polymorphic forms. In some embodiments, the 3-methoxy-N-[3-(2-methyl-2H-pyrazol-3-yl)-4-(2-morpholin-4-yl-ethoxy)-phenyl]-benzamide hydrate contains no more than about 1% of any other polymorphic forms.

In some embodiments, the 3-methoxy-N-[3-(2-methyl-2H-pyrazol-3-yl)-4-(2-morpholin-4-yl-ethoxy)-phenyl]-benzamide hydrate has a chemical purity of greater than about 95%. In some embodiments, the 3-methoxy-N-[3-(2-methyl-2H-pyrazol-3-yl)-4-(2-morpholin-4-yl-ethoxy)-phenyl]-benzamide hydrate has a chemical purity of greater than about 98%. In some embodiments, the 3-methoxy-N-[3-(2-methyl-2H-pyrazol-3-yl)-4-(2-morpholin-4-yl-ethoxy)-phenyl]-benzamide hydrate has a chemical purity of greater than about 99%.

In some embodiments, the (4-(2-(4-(3-methoxybenzamido)-2-(1-methyl-1H-pyrazol-5-yl)phenoxy)ethyl)morpholin-4-ium carboxyformate ethanol solvate contains no more than about 50% of any other polymorphic forms. In some embodiments, the (4-(2-(4-(3-methoxybenzamido)-2-(1-methyl-1H-pyrazol-5-yl)phenoxy)ethyl)morpholin-4-ium carboxyformate ethanol solvate contains no more than about 10% of any other polymorphic forms. In some embodiments, the (4-(2-(4-(3-methoxybenzamido)-2-(1-methyl-1H-pyrazol-5-yl)phenoxy)ethyl)morpholin-4-ium carboxyformate ethanol solvate contains no more than about 5% of any other polymorphic forms. In some embodiments, the (4-(2-(4-(3-methoxybenzamido)-2-(1-methyl-1H-pyrazol-5-yl)phenoxy)ethyl)morpholin-4-ium carboxyformate ethanol solvate contains no more than about 1% of any other polymorphic forms.

In some embodiments, the (4-(2-(4-(3-methoxybenzamido)-2-(1-methyl-1H-pyrazol-5-yl)phenoxy)ethyl)morpholin-4-ium carboxyformate ethanol solvate has a chemical purity of greater than about 95%. In some embodiments, the (4-(2-(4-(3-methoxybenzamido)-2-(1-methyl-1H-pyrazol-5-yl)phenoxy)ethyl)morpholin-4-ium carboxyformate ethanol solvate has a chemical purity of greater than about 98%. In some embodiments, the (4-(2-(4-(3-methoxybenzamido)-2-

(1-methyl-1H-pyrazol-5-yl)phenoxy)ethyl)morpholin-4-ium carboxyformate ethanol solvate has a chemical purity of greater than about 99%.

Also provided is a method for the preparation of 3-methoxy-N-[3-(2-methyl-2H-pyrazol-3-yl)-4-(2-morpholin-4-yl-ethoxy)-phenyl]-benzamide hydrate or a pharmaceutically acceptable salt thereof.

3-Methoxy-N-[3-(2-methyl-2H-pyrazol-3-yl)-4-(2-morpholin-4-yl-ethoxy)-phenyl]-benzamide hydrate can be prepared by any of the suitable procedures in the art for preparing crystalline polymorphs. In some embodiments, 3-methoxy-N-[3-(2-methyl-2H-pyrazol-3-yl)-4-(2-morpholin-4-yl-ethoxy)-phenyl]-benzamide hydrate can be prepared by a process comprising:

adding aqueous base to a solution of 4-(2-(4-(3-methoxybenzamido)-2-(1-methyl-1H-pyrazol-5-yl)phenoxy)ethyl)morpholin-4-ium chloride; and collecting the 3-methoxy-N-[3-(2-methyl-2H-pyrazol-3-yl)-4-(2-morpholin-4-yl-ethoxy)-phenyl]-benzamide hydrate.

In some embodiments, the aqueous base comprises aqueous sodium hydroxide. In some embodiments, the aqueous base comprises 1 N sodium hydroxide. In some embodiments, aqueous base is added until the mixture has a pH of ~8. In some embodiments, the 3-methoxy-N-[3-(2-methyl-2H-pyrazol-3-yl)-4-(2-morpholin-4-yl-ethoxy)-phenyl]-benzamide hydrate is collected by filtration.

In some embodiments, the method for the preparation of (4-(2-(4-(3-methoxybenzamido)-2-(1-methyl-1H-pyrazol-5-yl)phenoxy)ethyl)morpholin-4-ium carboxyformate ethanol solvate comprises:

adding ethanol and oxalic acid to 3-methoxy-N-[3-(2-methyl-2H-pyrazol-3-yl)-4-(2-morpholin-4-yl-ethoxy)-phenyl]-benzamide; and collecting the (4-(2-(4-(3-methoxybenzamido)-2-(1-methyl-1H-pyrazol-5-yl)phenoxy)ethyl)morpholin-4-ium carboxyformate ethanol solvate.

In some embodiments, the ethanol comprises 95% aqueous ethanol. In some embodiments, less than an equivalent, such as about 0.5 equivalent, of oxalic acid is used. In some embodiments, the 3(4-(2-(4-(3-methoxybenzamido)-2-(1-methyl-1H-pyrazol-5-yl)phenoxy)ethyl)morpholin-4-ium carboxyformate ethanol solvate is collected by filtration.

Also provided is a product of any of the methods of preparation described herein.

In some embodiments, the solvates described herein further comprises a detectable amount of at least one organic solvent. In some embodiments, the at least one organic solvent corresponds to a solvent used during the preparation of 3-methoxy-N-[3-(2-methyl-2H-pyrazol-3-yl)-4-(2-morpholin-4-yl-ethoxy)-phenyl]-benzamide or a pharmaceutically acceptable salt thereof.

Provided are compositions comprising at least one solvate described herein. In some embodiments, the compositions described herein comprise at least about 1, about 5, about 10, about 20, about 30, or about 40% by weight of at least one solvate described herein. In some embodiments, the compositions described herein comprise at least about 1, about 5, about 10, about 20, about 30, or about 40% by weight of 3-methoxy-N-[3-(2-methyl-2H-pyrazol-3-yl)-4-(2-morpholin-4-yl-ethoxy)-phenyl]-benzamide hydrate. In some embodiments, the compositions described herein comprise at least about 1, about 5, about 10, about 20, about 30, or about 40% by weight of a hydrate of (4-(2-(4-(3-methoxybenzamido)-2-(1-methyl-1H-pyrazol-5-yl)phenoxy)ethyl)morpholin-4-ium carboxyformate ethanol solvate.

In some embodiments, the solvates described herein have activity as $5\text{-}HT_{2A}$ receptor modulators. Accordingly, the solvates described herein may be used in methods of modulating the $5\text{-}HT_{2A}$ receptor by contacting the receptor with at least one solvate described herein. In some embodiments, at least one solvate described herein can be used to modulate $5\text{-}HT_{2A}$ receptors in an individual in need of such modulation by administering a therapeutically effective amount of at least one solvate described herein or a pharmaceutical composition thereof.

Also provided are methods of treating diseases associated with the $5\text{-}HT_{2A}$ receptor in an individual (e.g., patient) by administering to the individual in need of such treatment a therapeutically effective amount or dose of at least one solvate described herein or a pharmaceutical composition thereof. Example diseases can include any disease, disorder or condition that is directly or indirectly linked to expression or activity of the $5\text{-}HT_{2A}$ receptor.

Example diseases include platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders, progressive multifocal leukoencephalopathy, and the like.

Also provided are methods of treating coronary artery disease, myocardial infarction, transient ischemic attack, angina, stroke, and atrial fibrillation comprising administering to a patient in need thereof a therapeutically effective amount of at least one solvate described herein or a pharmaceutical composition thereof.

Also provided are methods of treating a condition associated with platelet aggregation comprising administering to a patient in need thereof a therapeutically effective amount of at least one solvate described herein or a pharmaceutical composition thereof.

Also provided are methods of reducing the risk of blood clot formation in an angioplasty or coronary bypass surgery individual comprising administering to a patient in need thereof a therapeutically effective amount of at least one solvate described herein or a pharmaceutical composition thereof.

Also provided are methods of reducing the risk of blood clot formation in an individual suffering from atrial fibrillation comprising administering to a patient a therapeutically effective amount of at least one solvate described herein or a pharmaceutical composition thereof.

Also provided are methods of treating a sleep disorder comprising administering to a patient a therapeutically effective amount of at least one solvate described herein or a pharmaceutical composition thereof.

Also provided are methods of treating a dyssomnia comprising administering to a patient a therapeutically effective amount of at least one solvate described herein or a pharmaceutical composition thereof.

Also provided are methods of treating a parasomnia comprising administering to a patient a therapeutically effective amount of at least one solvate described herein or a pharmaceutical composition thereof.

Also provided are methods of treating a diabetic-related disorder comprising administering to a patient a therapeutically effective amount of at least one solvate described herein or a pharmaceutical composition thereof.

Also provided are methods of treating progressive multifocal leukoencephalopathy comprising administering to a patient a therapeutically effective amount of at least one solvate described herein or a pharmaceutical composition thereof.

Also provided are methods of treating hypertension comprising administering to a patient a therapeutically effective amount of at least one solvate described herein or a pharmaceutical composition thereof.

Also provided are methods of treating pain comprising administering to a patient a therapeutically effective amount of at least one solvate described herein or a pharmaceutical composition thereof.

In some embodiments, the above methods further comprise the step of identifying a patient, where the patient is in need of treatment for the particular disease being treated, wherein the identifying step is performed prior to administration to the patient of the therapeutically effective amount of at least one solvate described herein or a pharmaceutical composition thereof.

Also provided is at least one solvate described herein or a pharmaceutical composition thereof for use in a method of treatment of the human or animal body by therapy.

Also provided is a pharmaceutical composition comprising at least one solvate described herein and at least one pharmaceutically acceptable carrier for use in a method of treatment of the human or animal body by therapy.

Also provided is at least one solvate described herein or a pharmaceutical composition thereof for use in a method of treatment of a $5HT_{2A}$-related disorder.

Also provided is at least one solvate described herein or a pharmaceutical composition thereof in a method of treatment of platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders or progressive multifocal leukoencephalopathy.

Also provided is at least one solvate described herein or a pharmaceutical composition thereof for use in a method of treatment of coronary artery disease, myocardial infarction, transient ischemic attack, angina, stroke or atrial fibrillation.

Also provided is at least one solvate described herein or a pharmaceutical composition thereof for use in a method for treating a condition associated with platelet aggregation.

Also provided is at least one solvate described herein or a pharmaceutical composition thereof for use in a method for reducing the risk of blood clot formation in an angioplasty or coronary bypass surgery.

Also provided is at least one solvate described herein or a pharmaceutical composition thereof for use in a method for reducing the risk of blood clot formation in an individual suffering from atrial fibrillation.

Also provided is at least one solvate described herein or a pharmaceutical composition thereof for use in a method for treating a sleep disorder.

Also provided is at least one solvate described herein or a pharmaceutical composition thereof for use in a method for treating a parasomnia.

Also provided is at least one solvate described herein or a pharmaceutical composition thereof for use in a method for treating a dyssomnia.

Also provided is at least one solvate described herein or a pharmaceutical composition thereof for use in a method for treating a diabetic-related disorder.

Also provided is at least one solvate described herein or a pharmaceutical composition thereof for use in a method for treating progressive multifocal.

Also provided is at least one solvate described herein or a pharmaceutical composition thereof for use in a method for treating hypertension.

Also provided is at least one solvate described herein or a pharmaceutical composition thereof for use in a method for treating pain.

Also provided is at least one solvate described herein for the manufacture of a medicament for treating a $5HT_{2A}$-related disorder.

Also provided is at least one solvate described herein for the manufacture of a medicament for treating platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders, progressive multifocal leukoencephalopathy.

Also provided is at least one solvate described herein for the manufacture of a medicament for treating coronary artery disease, myocardial infarction, transient ischemic attack, angina, stroke, and atrial fibrillation.

Also provided is at least one solvate described herein for the manufacture of a medicament for treating condition associated with platelet aggregation.

Also provided is at least one solvate described herein for the manufacture of a medicament for reducing the risk of blood clot formation in an angioplasty or coronary bypass surgery individual.

Also provided is at least one solvate described herein for the manufacture of a medicament for reducing the risk of blood clot formation in an individual suffering from atrial fibrillation.

Also provided is at least one solvate described herein for the manufacture of a medicament for treating a sleep disorder.

Also provided is at least one solvate described herein for the manufacture of a medicament for treating a dyssomnia.

Also provided is at least one solvate described herein for the manufacture of a medicament for treating a parasomnia.

Also provided is at least one solvate described herein for the manufacture of a medicament for treating a diabetic-related disorder.

Also provided is at least one solvate described herein for the manufacture of a medicament for treating progressive multifocal leukoencephalopathy.

Also provided is at least one solvate described herein for the manufacture of a medicament for treating hypertension.

Also provided is at least one solvate described herein for the manufacture of a medicament for treating pain.

In addition to the foregoing beneficial uses for the modulators of $5\text{-}HT_{2A}$ receptor activity disclosed herein, the solvates disclosed herein are believed to be useful in the treatment of several additional diseases and disorders, and in the amelioration of symptoms thereof. Without limitation, these include the following:

Antiplatelet Therapies (Conditions Related to Platelet Aggregation):

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction (heart attack), the heart muscle does not receive enough oxygen-rich blood as a result of a blockage in the coronary blood vessels. If taken while an attack is in progress or immediately afterward (preferably within 30 minutes), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes.

Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

5-$HT_{2A}$ receptors are expressed on smooth muscle of blood vessels and 5-HT secreted by activated platelets causes vasoconstriction as well as activation of additional platelets during clotting. There is evidence that a 5-$HT_{2A}$ inverse agonist will inhibit platelet aggregation and thus be a potential treatment as an antiplatelet therapy (see Satimura, K, et al., Clin Cardiol 2002 Jan. 25 (1):28-32; and Wilson, H. C et al., Thromb Haemost 1991 Sep. 2; 66(3):355-60).

5-$HT_{2A}$ inverse agonists can be used to treat, for example, claudication or peripheral artery disease as well as cardiovascular complications (see Br. Med. J. 298: 424-430, 1989), Arterial thrombosis (see, Pawlak, D. et al. Thrombosis Research 90: 259-270, 1998), atherosclerosis (see, Hayashi, T. et al. Atherosclerosis 168: 23-31, 2003), vasoconstriction, caused by serotonin (see, Fujiwara, T. and Chiba, S. Journal of Cardiovascular Pharmacology 26: 503-510, 1995), restenosis of arteries following angioplasty or stent placement (see, Fujita, M. et al. Am Heart J. 145:e16 2003). It can also be used alone or in combination with thrombolytic therapy, for example, tPA (see, Yamashita, T. et al. Haemostasis 30:321-332, 2000), to provide cardioprotection following MI or postischemic myocardial dysfunction (see, Muto, T. et al. Mol. Cell. Biochem. 272: 119-132, 2005) or protection from ischemic injury during percutaneous coronary intervention (see, Horibe, E. Circulation Research 68: 68-72, 2004), and the like, including complications resulting therefrom.

5-$HT_{2A}$ inverse antagonists can increase circulating adiponectin in patients, suggesting that they would also be useful in protecting patients against indications that are linked to adiponectin, for example, myocardial ischemia reperfusion injury and artherosclerosis (see Nomura, Shosaku, et al. Blood Coagulation and Fibrinolysis 2005, 16, 423-428).

The solvates disclosed herein may provide beneficial improvement in microcirculation to patients in need of antiplatelet therapy by antagonizing the vasoconstrictive products of the aggregating platelets in, for example and not limited to the indications described above. Accordingly, also provided are methods for reducing platelet aggregation in a patient in need thereof comprising administering to the patient at least one solvate disclosed herein or a pharmaceutical composition thereof. Also provided are methods for treating coronary artery disease, myocardial infarction, transient ischemic attack, angina, stroke, atrial fibrillation, or a symptom of any of the foregoing in a patient in need of the treatment, comprising administering to the patient at least one solvate described herein or a pharmaceutical composition thereof.

Also provided are methods for reducing risk of blood clot formation in an angioplasty or coronary bypass surgery patient, or a patient suffering from atrial fibrillation, comprising administering to the patient at least one solvate described herein or a pharmaceutical composition thereof at a time where such risk exists.

Asthma

5-HT (5-hydroxytryptamine) has been linked to the pathophysiology of acute asthma (see Cazzola, M. and Matera, M. G., TIPS, 2000, 21, 13; and De Bie, J. J. et al., British J. Pharm., 1998, 124, 857-864). The solvates described herein may be useful in the treatment of asthma, and the treatment of the symptoms thereof. Accordingly, also provided are methods for treating asthma in a patient in need of the treatment, comprising administering to the patient at least one solvate described herein or a pharmaceutical composition thereof. Also provided are methods for treating a symptom of asthma in a patient in need of the treatment, comprising administering to the patient at least one solvate described herein or a pharmaceutical composition thereof.

Agitation

Agitation is a well-recognized behavioral syndrome with a range of symptoms, including hostility, extreme excitement, poor impulse control, tension and uncooperativeness (See Cohen-Mansfield J, and Billig, N., (1986), Agitated Behaviors in the Elderly. I. A Conceptual Review. J Am Geriatr Soc 34(10): 711-721).

Agitation is a common occurrence in the elderly and often associated with dementia such as those caused by Alzheimer's disease, Lewy Body, Parkinson's, and Huntington's, which are degenerative diseases of the nervous system and by diseases that affect blood vessels, such as stroke, or multi-infarct dementia, which is caused by multiple strokes in the brain can also induce dementia. Alzheimer's disease accounts for approximately 50 to 70% of all dementias (See Koss E, et al., (1997), Assessing patterns of agitation in Alzheimer's disease patients with the Cohen-Mansfield Agitation Inventory. The Alzheimer's Disease Cooperative Study Alzheimer Dis Assoc Disord 11(suppl 2):S45-S50).

An estimated five percent of people aged 65 and older and up to 20 percent of those aged 80 and older are affected by dementia; of these sufferers, nearly half exhibit behavioral disturbances, such as agitation, wandering and violent outbursts.

Agitated behaviors can also be manifested in cognitively intact elderly people and by those with psychiatric disorders other than dementia.

Agitation is often treated with antipsychotic medications such as haloperidol in nursing home and other assisted care settings. There is emerging evidence that agents acting at the $5\text{-HT}_{2A}$ receptors in the brain have the effects of reducing agitation in patients, including Alzheimer's dementia (See Katz, I. R., et al., J Clin Psychiatry 1999 February, 60(2):107-115; and Street, J. S., et al., Arch Gen Psychiatry 2000 October, 57(10):968-976).

The solvates described herein may be useful for treating agitation and symptoms thereof. Thus, provided are methods for treating agitation in a patient in need of such treatment comprising administering to the patient at least one solvate described herein or a pharmaceutical composition thereof. In some embodiments, the agitation is due to a psychiatric disorder other than dementia. Also provided are methods for treatment of agitation or a symptom thereof in a patient suffering from dementia comprising administering to the patient at least one solvate described herein or a pharmaceutical composition thereof. In some embodiments of such methods, the dementia is due to a degenerative disease of the nervous system, for example and without limitation, Alzheimer's disease, Lewy Body, Parkinson's disease, and Huntington's disease, or dementia due to diseases that affect blood vessels, including, without limitation, stroke and multi-infarct dementia. Also provided are methods for treating agitation or a symptom thereof in a patient in need of such treatment, where the patient is a cognitively intact elderly patient, comprising administering to the patient at least one solvate described herein or a pharmaceutical composition thereof.

Add-On Therapy to Haloperidol in the Treatment of Schizophrenia and Other Disorders:

Schizophrenia is a psychopathic disorder of unknown origin, which usually appears for the first time in early adulthood and is marked by a number of characteristics, psychotic symptoms, progression, phasic development and deterioration in social behavior and professional capability in the region below the highest level ever attained. Characteristic psychotic symptoms are disorders of thought content (multiple, fragmentary, incoherent, implausible or simply delusional contents or ideas of persecution) and of mentality (loss of association, flight of imagination, incoherence up to incomprehensibility), as well as disorders of perceptibility (hallucinations), of emotions (superficial or inadequate emotions), of self-perception, of intentions and impulses, of inter-human relationships, and finally psychomotoric disorders (such as catatonia). Other symptoms are also associated with this disorder. (See, American Statistical and Diagnostic Handbook).

Haloperidol (Haldol) is a potent dopamine $D_2$ receptor antagonist. It is widely prescribed for acute schizophrenic symptoms, and is very effective for the positive symptoms of schizophrenia. However, Haldol is not effective for the negative symptoms of schizophrenia and may actually induce negative symptoms as well as cognitive dysfunction. In some embodiments, adding a $5\text{-HT}_{2A}$ inverse agonist concomitantly with Haldol may provide benefits including the ability to use a lower dose of Haldol without losing its effects on positive symptoms, while reducing or eliminating its inductive effects on negative symptoms, and prolonging relapse to the patient's next schizophrenic event.

Haloperidol is used for treatment of a variety of behavioral disorders, drug induced psychosis, excitative psychosis, Gilles de la Tourette's syndrome, manic disorders, psychosis (organic and NOS), psychotic disorder, psychosis, schizophrenia (acute, chronic and NOS). Further uses include in the treatment of infantile autism, huntington's chorea, and nausea and vomiting from chemotherapy and chemotherapeutic antibodies. Administration of $5\text{-HT}_{2A}$ inverse agonists disclosed herein with haloperidol also may provide benefits in these indications.

Also provided are methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient a dopamine $D_2$ receptor antagonist and at least one solvate described herein or a pharmaceutical composition thereof.

Also provided are methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient haloperidol and at least one solvate described herein or a pharmaceutical composition thereof.

Also provided are methods for treating infantile autism, huntington's chorea, or nausea and vomiting from chemotherapy or chemotherapeutic antibodies comprising administering to the patient a dopamine $D_2$ receptor antagonist and at least one solvate described herein or a pharmaceutical composition thereof.

Also provided are methods for treating infantile autism, huntington's chorea, or nausea and vomiting from chemotherapy or chemotherapeutic antibodies comprising administering to the patient haloperidol and at least one solvate described herein or a pharmaceutical composition thereof.

Also provided are methods for treating schizophrenia in a patient in need of the treatment comprising administering to the patient a dopamine $D_2$ receptor antagonist and at least one solvate described herein or a pharmaceutical composition thereof. Preferably, the dopamine $D_2$ receptor antagonist is haloperidol.

The administration of the dopamine $D_2$ receptor antagonist can be concomitant with administration of the at least one solvate described herein or a pharmaceutical composition thereof, or they can be administered at different times. Those of skill in the art will easily be able to determine appropriate dosing regimes for the most efficacious reduction or elimination of deleterious haloperidol effects. In some embodiments, haloperidol and the at least one solvate described herein or a pharmaceutical composition thereof are administered in a single dosage form, and in other embodiments, they are administered in separate dosage forms.

Also provided are methods of alleviating negative symptoms of schizophrenia induced by the administration of haloperidol to a patient suffering from schizophrenia, comprising administering to the patient at least one solvate described herein or a pharmaceutical composition thereof.

Sleep Disorders

It is reported in the National Sleep Foundation's 2002 Sleep In America Poll, more than one-half of the adults surveyed (58%) report having experienced one or more symptoms of insomnia at least a few nights a week in the past year.

Additionally, about three in ten (35%) say they have experienced insomnia-like symptoms every night or almost every night.

The normal sleep cycle and sleep architecture can be disrupted by a variety of organic causes as well as environmental influences. According to the International Classification of Sleep Disorders, there are over 80 recognized sleep disorders. Of these, at least one solvate described herein or a pharmaceutical composition thereof may be effective, for example, in any one or more of the following sleep disorders (ICSD—International Classification of Sleep Disorders: Diagnostic and Coding Manual. *Diagnostic Classification Steering Committee*, American Sleep Disorders Association, 1990):

Dyssomnias
Intrinsic Sleep Disorders:

Psychophysiological insomnia, Sleep state misperception, Idiopathic insomnia, Obstructive sleep apnea syndrome, Central sleep apnea syndrome, Central alveolar hypoventilation syndrome, Periodic limb movement disorder, Restless leg syndrome and Intrinsic sleep disorder NOS.

Extrinsic Sleep Disorders:

Inadequate sleep hygiene, Environmental sleep disorder, Altitude insomnia, Adjustment sleep disorder, Insufficient sleep syndrome, Limit-setting sleep disorder, SleepOnset association disorder, Nocturnal eating (drinking) syndrome, Hypnotic dependent sleep disorder, Stimulant-dependent sleep disorder, Alcohol-dependent sleep disorder, Toxin-induced sleep disorder and Extrinsic sleep disorder NOS.

Circadian Rhythm Sleep Disorders:

Time zone change (jet lag) syndrome, Shift work sleep disorder, Irregular sleep-wake pattern, Delayed sleep phase syndrome, Advanced sleep phase syndrome, Non-24-hour sleep-wake disorder and Circadian rhythm sleep disorder NOS.

Parasomnias

Arousal Disorders:

Confusional arousals, Sleepwalking and Sleep terrors.

Sleep-Wake Transition Disorders:

Rhythmic movement disorder, Sleep starts, Sleep talking and Nocturnal leg cramps.

Sleep Disorders Associated with Medical/Psychiatric Disorders

Associated with Mental Disorders:

Psychoses, Mood disorders, Anxiety disorders, Panic disorders and Alcoholism.

Associated with Neurological Disorders:

Cerebral degenerative disorders, Dementia, Parkinsonism, Fatal familial insomnia, Sleep-related epilepsy, Electrical status epilepticus of sleep and Sleep-related headaches.

Associated with Other Medical Disorders:

Sleeping sickness, Nocturnal cardiac ischemia, Chronic obstructive pulmonary disease, Sleep-related asthma, Sleep-related gastroesophageal reflux, Peptic ulcer disease, Fibrositis syndrome, Osteoarthritis, Rheumatoid arthritis, Fibromyalgia and Post-surgical.

The effects of sleep deprivation are more than excessive daytime sleepiness. Chronic insomniacs report elevated levels of stress, anxiety, depression and medical illnesses (National Institutes of Health, National Heart, Lung, and Blood Institute, *Insomnia Facts Sheet*, October 1995). Preliminary evidence suggests that having a sleep disorder that causes significant loss of sleep may contribute to increased susceptibility to infections due to immunosuppression, cardiovascular complications such as hypertension, cardiac arrhythmias, stroke, and myocardial infarction, compromised glucose tolerance, increased obesity and metabolic syndrome. The solvates described herein may be useful to prevent or alleviate these complications by improving sleep quality.

The most common class of medications for the majority of sleep disorders are the benzodiazepines, but the adverse effect profile of benzodiazepines include daytime sedation, diminished motor coordination, and cognitive impairments. Furthermore, the National Institutes of Health Consensus conference on Sleeping Pills and Insomnia in 1984 have developed guidelines discouraging the use of such sedative-hypnotics beyond 4-6 weeks because of concerns raised over drug misuse, dependency, withdrawal and rebound insomnia. Therefore, it is desirable to have a pharmacological agent for the treatment of insomnia, which is more effective and/or has fewer side effects than those currently used. In addition, benzodiazepines are used to induce sleep, but have little to no effect on the maintenance of sleep, sleep consolidation or slow wave sleep. Therefore, sleep maintenance disorders are not currently well treated.

Clinical studies with agents of a similar mechanism of action as those described herein have demonstrated significant improvements on objective and subjective sleep parameters in normal, healthy volunteers as well as patients with sleep disorders and mood disorders [Sharpley A L, et al. Slow Wave Sleep in Humans: Role of 5-HT$_{2A}$ and 5HT$_{2C}$ Receptors. *Neuropharmacology*, 1994, Vol. 33(3/4):467-71; Winokur A, et al. Acute Effects of Mirtazapine on Sleep Continuity and Sleep Architecture in Depressed Patients: A Pilot Study. *Soc of Biol Psych*, 2000, Vol. 48:75-78; and Landolt H P, et al. Serotonin-2 Receptors and Human Sleep: Effect of Selective Antagonist on EEG Power Spectra. *Neuropsychopharmacology*, 1999, Vol. 21(3):455-66].

Some sleep disorders are sometimes found in conjunction with other conditions and accordingly those conditions may be treatable by at least one solvate described herein or a pharmaceutical composition thereof. For example, but not limited to, patients suffering from mood disorders typically suffer from a sleep disorder that may be treatable by at least one solvate described herein or a pharmaceutical composition thereof. Having one pharmacological agent which treats two or more existing or potential conditions may be more cost effective, may lead to better compliance and may have fewer side effects than taking two or more agents.

Also provided are methods for treating Sleep Disorders. Also provided are pharmaceutical agent, which may be useful in treating two or more conditions wherein one of the conditions is a sleep disorder. The solvates described herein may be used alone or in combination with a mild sleep inducer (i.e. antihistamine).

Sleep Architecture:

Sleep comprises two physiological states: Non rapid eye movement (NREM) and rapid eye movement (REM) sleep. NREM sleep consists of four stages, each of which is characterized by progressively slower brain wave patterns, with the slower patterns indicating deeper sleep. So called delta sleep, stages 3 and 4 of NREM sleep, is the deepest and most refreshing type of sleep. Many patients with sleep disorders are unable to adequately achieve the restorative sleep of stages 3 and 4. In clinical terms, patients' sleep patterns are described as fragmented, meaning the patient spends a lot of time alternating between stages 1 and 2 (semi-wakefulness) and being awake and very little time in deep sleep. As used herein, the term "fragmented sleep architecture" means an individual, such as a sleep disorder patient, spends the majority of their sleep time in NREM sleep stages 1 and 2, lighter periods of sleep from which the individual can be easily aroused to a Waking state by limited external stimuli. As a result, the individual cycles through frequent bouts of light sleep interrupted by frequent awakenings throughout the sleep period. Many sleep disorders are characterized by a fragmented sleep architecture. For example, many elderly patients with sleep complaints have difficulty achieving long bouts of deep refreshing sleep (NREM stages 3 and 4) and instead spend the majority of their sleep time in NREM sleep stages 1 and 2.

In contrast to fragmented sleep architecture, as used herein the term "sleep consolidation" means a state in which the number of NREM sleep bouts, particularly Stages 3 and 4, and the length of those sleep bouts are increased, while the number and length of waking bouts are decreased. In essence, the architecture of the sleep disorder patient is consolidated to a sleeping state with increased periods of sleep and fewer awakenings during the night and more time is spent in slow wave sleep (Stages 3 and 4) with fewer oscillation Stage 1 and 2 sleep. The solvates described herein may be effective in consolidating sleep patterns so that the patient with previously fragmented sleep can now achieve restorative, delta-wave sleep for longer, more consistent periods of time.

As sleep moves from stage 1 into later stages, heart rate and blood pressure drop, metabolic rate and glucose consumption fall, and muscles relax. In normal sleep architecture, NREM sleep makes up about 75% of total sleep time; stage 1 accounting for 5-10% of total sleep time, stage 2 for about 45-50%, stage 3 approximately 12%, and stage 4 13-15%. About 90 minutes after sleep onset, NREM sleep gives way to the first REM sleep episode of the night. REM makes up approximately 25% of total sleep time. In contrast to NREM sleep, REM sleep is characterized by high pulse, respiration, and blood pressure, as well as other physiological patterns similar to those seen in the active waking stage. Hence, REM sleep is also known as "paradoxical sleep." Sleep onset occurs during NREM sleep and takes 10-20 minutes in healthy young adults. The four stages of NREM sleep together with a REM phase form one complete sleep cycle that is repeated throughout the duration of sleep, usually four or five times. The cyclical nature of sleep is regular and reliable; a REM period occurs about every 90 minutes during the night. However, the first REM period tends to be the shortest, often lasting less than 10 minutes, whereas the later REM periods may last up to 40 minutes. With aging, the time between retiring and sleep onset increases and the total amount of night-time sleep decreases because of changes in sleep architecture that impair sleep maintenance as well as sleep quality. Both NREM (particularly stages 3 and 4) and REM sleep are reduced. However, stage 1 NREM sleep, which is the lightest sleep, increases with age.

As used herein, the term "delta power" means a measure of the duration of EEG activity in the 0.5 to 3.5 Hz range during NREM sleep and is thought to be a measure of deeper, more refreshing sleep. Delta power is hypothesized to be a measure of a theoretical process called Process S and is thought to be inversely related to the amount of sleep an individual experiences during a given sleep period. Sleep is controlled by homeostatic mechanisms; therefore, the less one sleeps the greater the drive to sleep. It is believed that Process S builds throughout the wake period and is discharged most efficiently during delta power sleep. Delta power is a measure of the magnitude of Process S prior to the sleep period. The longer one stays awake, the greater Process S or drive to sleep and thus the greater the delta power during NREM sleep. However, individuals with sleep disorders have difficulty achieving and maintaining delta wave sleep, and thus have a large build-up of Process S with limited ability to discharge this buildup during sleep. $5-HT_{2A}$ agonists tested preclinically and clinically mimic the effect of sleep deprivation on delta power, suggesting that subjects with sleep disorders treated with a $5-HT_{2A}$ inverse agonist or antagonist will be able to achieve deeper more refreshing sleep. These same effects have not been observed with currently marketed pharmacotherapies. In addition, currently marketed pharmacotherapies for sleep have side effects such as hangover effects or addiction that are associated with the GABA receptor. $5-HT_{2A}$ inverse agonists do not target the GABA receptor and so these side effects are not a concern.

Subjective and Objective Determinations of Sleep Disorders:

There are a number of ways to determine whether the onset, duration or quality of sleep (e.g. non-restorative or restorative sleep) is impaired or improved. One method is a subjective determination of the patient, e.g., do they feel drowsy or rested upon waking. Other methods involve the observation of the patient by another during sleep, e.g., how long it takes the patient to fall asleep, how many times does the patient wake up during the night, how restless is the patient during sleep, etc. Another method is to objectively measure the stages of sleep using polysomnography.

Polysomnography is the monitoring of multiple electrophysiological parameters during sleep and generally includes measurement of EEG activity, electroculographic activity and electromyographic activity, as well as other measurements. These results, along with observations, can measure not only sleep latency (the amount of time required to fall asleep), but also sleep continuity (overall balance of sleep and wakefulness) and sleep consolidation (percent of sleeping time spent in delta-wave or restorative sleep) which may be an indication of the quality of sleep.

There are five distinct sleep stages, which can be measured by polysomnography: rapid eye movement (REM) sleep and four stages of non-rapid eye movement (NREM) sleep (stages 1, 2, 3 and 4). Stage 1 NREM sleep is a transition from wakefulness to sleep and occupies about 5% of time spent asleep in healthy adults. Stage 2 NREM sleep, which is characterized by specific EEG waveforms (sleep spindles and K complexes), occupies about 50% of time spent asleep. Stages 3 and 4 NREM sleep (also known collectively as slow-wave sleep and delta-wave sleep) are the deepest levels of sleep and occupy about 10-20% of sleep time. REM sleep, during which the majority of vivid dreams occur, occupies about 20-25% of total sleep.

These sleep stages have a characteristic temporal organization across the night. NREM stages 3 and 4 tend to occur in the first one-third to one-half of the night and increase in duration in response to sleep deprivation. REM sleep occurs cyclically through the night. Alternating with NREM sleep about every 80-100 minutes. REM sleep periods increase in duration toward the morning. Human sleep also varies characteristically across the life span. After relative stability with large amounts of slow-wave sleep in childhood and early adolescence, sleep continuity and depth deteriorate across the adult age range. This deterioration is reflected by increased wakefulness and stage 1 sleep and decreased stages 3 and 4 sleep.

In addition, the solvates described herein may be useful for the treatment of the sleep disorders characterized by excessive daytime sleepiness such as narcolepsy. Inverse agonists at the serotonin $5-HT_{2A}$ receptor improve the quality of sleep at nighttime which can decrease excessive daytime sleepiness.

Also provided is the therapeutic use of at least one solvate described herein or a pharmaceutical composition thereof for the treatment of Sleep Disorders. The solvates described herein are potent inverse agonists at the serotonin $5-HT_{2A}$ receptor and may be effective in the treatment of Sleep Disorders by promoting one or more of the following: reducing the sleep onset latency period (measure of sleep induction), reducing the number of nighttime awakenings, and prolonging the amount of time in delta-wave sleep (measure of sleep quality enhancement and sleep consolidation) without effecting REM sleep. In addition, the solvates described herein can be effective either as a monotherapy or in combination with sleep inducing agents, for example but not limited to, antihistamines.

Diabetic-Related Pathologies:

Although hyperglycemia is the major cause for the pathogenesis of diabetic complications such as diabetic peripheral neuropathy (DPN), diabetic nephropathy (DN) and diabetic retinopathy (DR), increased plasma serotonin concentration in diabetic patients has also been implicated to play a role in disease progression (Pietraszek, M. H., et al. *Thrombosis Res.* 1992, 66(6), 765-74; and Andrzejewska-Buczko J, et al., *Klin Oczna.* 1996; 98(2), 101-4). Serotonin is believed to play a role in vasospasm and increased platelet aggregability. Improving microvascular blood flow is able to benefit diabetic complications.

A recent study by Cameron and Cotter in *Naunyn Schmiedebergs Arch Pharmacol.* 2003 June; 367(6):607-14, used a 5-$HT_{2A}$ antagonist experimental drug AT-1015, and other non-specific 5-$HT_{2A}$ antagonists including ritanserin and sarpogrelate. These studies found that all three drugs were able to produce a marked correction (82.6-99.7%) of a 19.8% sciatic motor conduction deficit in diabetic rats. Similarly, 44.7% and 14.9% reductions in sciatic endoneurial blood flow and saphenous sensory conduction velocity were completely reversed.

In a separate patient study, sarogrelate was evaluated for the prevention of the development or progression of diabetic nephropathy (Takahashi, T., et al., *Diabetes Res Clin Pract.* 2002 November; 58(2):123-9). In the trial of 24 months of treatment, sarpogrelate significantly reduced urinary albumin excretion level.

Glaucoma

Topical ocular administration of 5-HT2 receptor antagonists result in a decrease in intra ocular pressure (IOP) in monkeys (Chang et al., *J. Ocul Pharmacol* 1:137-147 (1985)) and humans (Mastropasqua et al., *Acta Ophthalmol Scand Suppl* 224:24-25 (1997)) indicating utility for similar compounds such as 5-$HT_{2A}$ inverse agonists in the treatment of ocular hypertension associated with glaucoma. The 5-HT2 receptor antagonist ketanserin (Mastropasqua supra) and sarpogrelate (Takenaka et al., *Investig Ophthalmol Vis Sci* 36:S734 (1995)) have been shown to significantly lower IOP in glaucoma patients.

Progressive Multifocal Leukoencephalopathy

Progressive multifocal leukoencephalopathy (PML) is a lethal demyelinating disease caused by an opportunistic viral infection of oligodendrocytes in immunocompromised patients. The causative agent is JC virus, a ubiquitous papovavirus that infects the majority of the population before adulthood and establishes a latent infection in the kidney. In immunocompromised hosts, the virus can reactivate and productively infect oligodendrocytes. This previously rare condition, until 1984 reported primarily in persons with underlying lymphoproliferative disorders, is now more common because it occurs in 4% of patients with AIDS. Patients usually present with relentlessly progressive focal neurologic defects, such as hemiparesis or visual field deficits, or with alterations in mental status. On brain MRI, one or more white matter lesions are present; they are hyperintense on T2-weighted images and hypointense on T1-weighted images. There is no mass effect, and contrast enhancement is rare. Diagnosis can be confirmed by brain biopsy, with demonstration of virus by in situ hybridization or immunocytochemistry. Polymerase chain reaction amplification of JC virus sequences from the CSF can confirm diagnosis without the need for biopsy [see, e.g., Antinori et al., *Neurology* (1997) 48:687-694; Berger and Major, *Seminars in Neurology* (1999) 19:193-200; and Portegies, et al., *Eur. J. Neurol.* (2004) 11:297-304]. Currently, there is no effective therapy. Survival after diagnosis is about 3 to 5 months in AIDS patients.

JC virus enters cells by receptor-mediated clathrin-dependent endocytosis. Binding of JC virus to human glial cells (e.g., oligodendrocytes) induces an intracellular signal that is critical for entry and infection by a ligand-inducible clathrin-dependent mechanism [Querbes et al., *J Virology* (2004) 78:250-256]. Recently, 5-$HT_{2A}$ was shown to be the receptor on human glial cells mediating infectious entry of JC virus by clathrin-dependent endocytosis [Elphick et al., *Science* (2004) 306:1380-1383]. 5-$HT_{2A}$ antagonists, including ketanserin and ritanserin, inhibited JC virus infection of human glial cells. Ketanserin and ritanserin have inverse agonist activity at 5-$HT_{2A}$.

5-$HT_{2A}$ antagonists including inverse agonists have been contemplated to be useful in the treatment of PML [Elphick et al., *Science* (2004) 306:1380-1383]. Prophylactic treatment of HIV-infected patients with 5-$HT_{2A}$ antagonists is envisioned to prevent the spread of JC virus to the central nervous system and the development of PML. Aggressive therapeutic treatment of patients with PML is envisioned to reduce viral spread within the central nervous system and prevent additional episodes of demyelination.

Also provided are methods for treating progressive multifocal leukoencephalopathy in a patient in need of such treatment, comprising administering to the patient at least one solvate described herein or a pharmaceutical composition thereof.

Hypertension

Serotonin has been observed to play an important role in the regulation of vascular tone, vasoconstriction, and pulmonary hypertension (see, Deuchar, G. et al. Pulm. Pharmacol. Ther. 18(1):23-31. 2005; and Marcos, E. et al. Circ. Res. 94(9):1263-70 2004). Ketanserin, a 5-HT2A inverse agonist, have been demonstrated to protect against circulatory shocks, intracranial hypertension, and cerebral ischemia during heatstroke (see, Chang, C. et al. Shock 24(4): 336-340 2005); and to stabilize blood pressure in spontaneously hypertensive rats (see, Miao, C. Clin. Exp. Pharmacol. Physiol. 30(3): 189-193). Mainserin, a 5-HT2A inverse agonist, has been shown to prevent DOCA-salt induced hypertension in rats (see, Silva, A. Eur, J. Pharmacol. 518(2-3): 152-7 2005).

Pain

5-HT2A inverse agonists are also effective for the treatment of pain. Sarpogrelate has been observed to provide a significant analgesic effect both on thermal induced pain in rats after intraperitoneal administration and on inflammatory pain in rats after either intrathecal or intraperitoneal administration (see, Nishiyama, T. Eur. J. Pharmacol. 516:18-22 2005). This same 5-HT2A inverse agonist in humans has been shown to be an effective treatment for lower back pain, leg pain and numbness associated with sciatica brought on by lumbar disc herniation (see, Kanayama, M. et al. J. Neurosurg: Spine 2:441-446 2005).

Also provided are pharmaceutical compositions comprising at least one solvate described herein and one or more pharmaceutically acceptable carriers.

In some embodiments, the at least one solvate is administered as a raw or pure chemical.

Also provided are pharmaceutical compositions comprising 3-methoxy-N-[3-(2-methyl-2H-pyrazol-3-yl)-4-(2-morpholin-4-yl-ethoxy)-phenyl]-benzamide hydrate and one or more pharmaceutically acceptable carriers.

Also provided are pharmaceutical compositions comprising (4-(2-(4-(3-methoxybenzamido)-2-(1-methyl-1H-pyrazol-5-yl)phenoxy)ethyl)morpholin-4-ium carboxyformate ethanol solvate and one or more pharmaceutically acceptable carriers.

Also provided is a method of producing a pharmaceutical composition comprising admixing at least one solvate described herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving at least one solvate described herein in a suitable liquid vehicle and filter sterilizing the solution before filling and sealing an appropriate vial or ampoule. These are just a few examples of the many appropriate methods well known in the art for preparing dosage forms.

Pharmaceutical compositions may be formulated using techniques well known to those in the art. Suitable pharmaceutically-acceptable carriers, outside those mentioned herein, are known in the art; for example, see Remington, *The Science and Practice of Pharmacy*, 20$^{th}$ Ed., 2000, Lippincott Williams & Wilkins, (Editors: Gennaro, A. R., et al.). The carrier(s) is be "acceptable" in the sense of being compatible with the other ingredients of the for compositions and not overly deleterious to the recipient thereof.

Pharmaceutical compositions include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The solvates described herein, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate. The active ingredient may also be administered by injection as a composition wherein, for example, saline, dextrose or water may be used as a suitable pharmaceutically acceptable carrier.

The solvates described herein can be used as active ingredients in pharmaceutical compositions, specifically as 5-HT$_{2A}$ receptor modulators. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the solvates described herein can vary within wide limits, as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the solvates described herein. Representative doses include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, or whether an acute or chronic disease state is being treated or prophylaxis is conducted or on whether further active compounds are administered in addition to the solvates described herein and as part of a drug combination. The dosage regimen for treating a disease condition with the solvates described herein is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods described herein.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The solvates described herein can be administrated in a wide variety of oral and parenteral dosage forms.

For preparing pharmaceutical compositions from the solvates described herein, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The solvates described herein may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the solvates described herein may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the solvates described herein or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the solvates described herein as an aerosol can be prepared by processes well-known to the person skilled in the art. For their preparation, for example, solutions or dispersions of the solvates described herein in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the solvates described herein will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethylcellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In some embodiments, tablets or capsules for oral administration and liquids for intravenous administration are used.

While the solvates described herein can be administered as the sole active pharmaceutical agent (i.e., mono-therapy), they can also be used in combination with other pharmaceutical agents (i.e., combination-therapy) for the treatment of the diseases/conditions/disorders described herein. Accordingly, also provided are methods of treatment of 5-$HT_{2A}$ serotonin receptor mediated disorders diseases comprising administering to an individual in need of such treatment a therapeutically-effective amount of at least one solvate described herein in combination with one or more additional pharmaceutical agent as described herein.

Suitable pharmaceutical agents that can be used in combination with the solvates described herein include other antiplatelet, antithrombotic or anticoagulant drugs, anti-arrhythmic agents, Cholesteryl ester transfer protein (CETP) inhibitors, Niacin or niacin analogs, Adenosine or adenosine analogs, Nitroglycerin or nitrates, prothrombolytic agents, and the like. Other pharmaceutical agents, including the agents set forth infra, are well known or will be readily apparent in light of the instant disclosure, to one of ordinary skill in the art.

The solvates described herein can also be used in combination with other antiplatelet, antithrombotic or anticoagulant drugs such as thrombin inhibitors, platelet aggregation inhibitors such as aspirin, clopidogrel (Plavix®), ticlopidine or CS-747 {i.e., acetic acid 5-[2-cyclopropyl-1-(2-fluorophenyl)-2-oxoethyl]-4,5,6,7-tetrahydrothieno[3,2-c]pyridin-2-yl ester and its active metabolite R-99224, (Z)-2-[1-[2-cyclopropyl-1(S)-(2-fluorophenyl)-2-oxoethyl]-4(R)-sulfanylpiperidin-3-ylidene]acetic acid}, abciximab (ReoPro®), eptifibatide (Integrilin®), tirofiban (Aggrastat®), warfarin, low molecular weight heparins (such as LOVENOX), GPIIb/GPIIIa blockers, PAI-1 inhibitors such as XR-330 [i.e., (3Z,6Z)-3-Benzylidene-6-(4-methoxybenzylidene)-1-methylpiperazine-2,5-dione] and T-686 [i.e., 3(E)-Benzylidene-4(E)-(3,4,5-trimethoxybenzylidene)pyrrolidine-2,5-dione], inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole (Persantine®) or cilostazol, PDE inhibitors in combination with thromboxane receptor antagonists/thromboxane A synthetase inhibitors (such as picotamide), serotonin-2-receptor antagonists (such as ketanserin), fibrinogen receptor antagonists, hypolipidemic agents, such as HMG-CoA reductase inhibitors, e.g., pravastatin, simvastatin, atorvastatin, fluvastatin, cerivastatin, AZ4522, and itavastatin (Nissan/Kowa); microsomal triglyceride transport protein inhibitors (such as disclosed in U.S. Pat. Nos. 5,739,135, 5,712,279 and 5,760,246), antihypertensive agents such as angiotensin-converting enzyme inhibitors (e.g., captopril, lisinopril or fosinopril); angiotensin-II receptor antagonists (e.g., irbesartan, losartan or valsartan); and/or ACE/NEP inhibitors (e.g., omapatrilat and gemopatrilat); β-blockers (such as propranolol, nadolol and carvedilol), PDE inhibitors in combination with aspirin, ifetroban, picotamide, ketanserin, or clopidogrel (Plavix®) and the like.

The solvates described herein can also be used in combination with anti-arrhythmic agents such as for atrial fibrillation, for example, amiodarone or dofetilide.

The solvates described herein can also be used in combination with Cholesteryl ester transfer protein (CETP) inhibitors for dislipidemia and atherosclerosis, Niacin or niacin analogs for dislipidemia and atherosclerosis, Adenosine or adenosine analogs for vasodilation, Nitroglycerin or nitrates for vasodilation.

The solvates described herein can be used in combination with prothrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like. The solvates described herein may also be used in combination with β-adrenergic agonists such as albuterol, terbutaline, formoterol, salmeterol, bitolterol, pilbuterol, or fenoterol; anticholinergics such as ipratropium bromide; anti-inflammatory corticosteroids such as beclomethasone, triamcinolone, budesonide, fluticasone, flunisolide or dexamethasone; and anti-inflammatory agents such as cromolyn, nedocromil, theophylline, zileuton, zafirlukast, monteleukast and pranleukast.

Suitable pharmaceutical agents that can be used in combination with solvates described herein include antiretrovirals [see, e.g., Turpin, *Expert Rev Anti Infect Ther* (2003) 1:97-128]. Some embodiments include methods of treatment of progressive multifocal leukoencephalopathy as described herein comprising administering to an individual in need of such treatment a therapeutically effective amount or dose of at least one solvate described herein in combination with at least one pharmaceutical agent selected from nucleoside reverse transcriptase inhibitors (for example, Retrovir®, Epivir®, Combivir®, Hivid®, Videx®, Trizvir®, Zerit®, Ziagen®, Vired®, Emtricitabine, DAPD, and the like), non-nucleoside reverse transcriptase inhibitors (for example, Virammune®, Rescriptor®, Sustiva®, GW687, DPC083, TMC 125, Emivirine, Capravirine, BMS 561390, UC-781 and other oxathiin carboxyanilides, SJ-3366, Alkenyldiarylmethane (ADAM), Tivirapine, Calanolide A, HBY097, Loviride, HEPT Family Derivatives, TIBO Derivatives, and the like), protease inhibitors (for example, Fortovase®, Invirase®, Novir®, Crixivan®, Viracep®, Ageberase®, Kaletra®, Atazanavir, Tipranavir, DMP450, and the like), inhibitors of HIV-cell interaction (for example, soluble CD4, toxin-conjugated CD4, monoclonal antibodies to CD4 or gp120, PRO 542, dextran sulfate, Rersobene, FP-23199, Cyanovirin-N, Zintevir (T30177, AR177), L-chicoric acid and derivatives, and the like), coreceptor inhibitors ligands (for example, R5, X4, modified ligands (R5), modified ligands (X4), and the like), coreceptor inhibitors X4 (for example, T22, T134, ALX40-4C, AMD3100, bycyclam derivatives, and the like), coreceptor inhibitors R5 (for example, TAK-779, SCH-C (SCH-351125), SCH-D (SCH-350634), NSC 651016, ONO Pharmaceutical, Merck, and the like), fusion inhibitors (for example, Fuzeon® (T-20, DP 178, enfuvritide) trimeris, T-1249, TMC125, and the like), integrase inhibitors (for example, 5CITEP, L731,988, L708,906, L-870,812, S-1360, and the like), NCp7 nucleocapsid Zn finger inhibitors (for example, NOBA, DIBA, dithianes, PD-161374, pyridinioalkanoyl thioesters (PATES), azodicarbonamide (ADA), cyclic 2,2 dithio bisbenzamide, and the like), RNase H inhibitors (for example, BBHN, CPHM PD-26388, and the like), Tat inhibitors (for example, dominant negative mutants, Ro24-7429, Ro5-3335, and the like), Rev inhibitors (for example, dominant negative mutants, Leptomycin B, PKF050-638, and the like), transcriptional inhibitors (for example, Temacrazine, K-12 and K-37, EM2487, and the like), inhibitors of HIV assembly/maturation (for example, CAP-1 and CAP-2, and the like), and pharmaceutical agents directed to cellular anti-HIV targets (for example, LB6-B275 and HRM1275, Cdk9 inhibitors, and the like).

In a certain embodiment, a solvates described herein can be used in conjunction with highly active antiretroviral therapy (HAART). When antiretroviral drugs are used in combinations of three or four drugs, this treatment is called HAART [see, e.g., Portegies, et al., *Eur. J. Neurol.* (2004) 11:297-304].

In some embodiment, the combination of a solvate described herein and pharmaceutical agent can be prepared by mixing the respective active components either all together or independently with a pharmaceutically acceptable carrier, excipient, binder, diluent, etc. as described herein, and administering the mixture or mixtures either orally or non-orally as a pharmaceutical composition(s). When a solvate described herein is administered as a combination therapy with another active compound each can be formulated as separate pharmaceutical compositions given at the same time or at different times. Alternatively, in some embodiments, pharmaceutical compositions comprise at least one solvate described herein and the pharmaceutical agent(s) as a single pharmaceutical composition.

In some embodiments, a method of producing a pharmaceutical composition for "combination-therapy" comprises admixing at least one solvate described herein, together with at least one known pharmaceutical agent as described herein and a pharmaceutically acceptable carrier.

It is noted that when the 5-$HT_{2A}$ receptor modulators are utilized as active ingredients in a pharmaceutical composition, these are not intended for use only in humans, but in other non-human mammals as well. Indeed, recent advances in the area of animal health-care mandate that consideration be given for the use of active agents, such as 5-$HT_{2A}$ receptor modulators, for the treatment of a 5-$HT_{2A}$ mediated disease or disorder in domestic animals (e.g., cats and dogs) and in other livestock animals (e.g., such as cows, chickens, fish, etc.). Those of ordinary skill in the art are readily credited with understanding the utility of such solvates described herein in such settings.

For the avoidance of any doubt, it is understood that those embodiments which refer to methods of treatment or other uses of the solvates described herein further embrace pharmaceutical compositions comprising the solvates described herein, as well as combinations of other pharmaceutical agents with solvates and pharmaceutical compositions described herein.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

4-(2-(4-(3-Methoxybenzamido)-2-(1-methyl-1H-pyrazol-5-yl)phenoxy)ethyl)morpholin-4-ium chloride Anhydrous 4-(2-(4-(3-methoxybenzamido)-2-(1-methyl-1H-pyrazol-5-yl)phenoxy)ethyl)morpholin-4-ium chloride can be prepared as described in WO 2007/136689.

A slurry of anhydrous 4-(2-(4-(3-methoxybenzamido)-2-(1-methyl-1H-pyrazol-5-yl)phenoxy)ethyl)morpholin-4-ium chloride in water was stirred at ambient/stir plate temperature (about 26-28° C.) for ~3 days. The anhydrous form was recovered.

Example 2

3-Methoxy-N-[3-(2-methyl-2H-pyrazol-3-yl)-4-(2-morpholin-4-yl-ethoxy)-phenyl]-benzamide hydrate 100 mg of 4-(2-(4-(3-methoxybenzamido)-2-(1-methyl-1H-pyrazol-5-yl)phenoxy)ethyl)morpholin-4-ium chloride were added to 3 mL of $H_2O$ in a 4 mL vial. The solution was stirred until it became clear. 225 µL of 1 N NaOH was added to the vial to reach a pH of ~8. A white precipitate formed. The solution was stirred for 1 hour at room temperature. The crystalline materials formed on the side of the vial were scraped off, and the solution was filtered using centrifuge tube filters. The material was dried overnight in the hood.

The sample was characterized by an X'Pert PRO MPD powder diffractometer (PANalytical, Inc.; EQ0233) with a Cu source set at 45 kV and 40 mA, Cu(Kα) radiation and an X'Celerator detector. Briefly, samples were added to a sample holder and smoothed flat with a spatula and weigh paper. While the samples were spinning, X-ray diffractograms were obtained by a 12-minute scan over the (2θ) range 5-40°.

FIG. 1 shows the PXRD pattern of 3-methoxy-N-[3-(2-methyl-2H-pyrazol-3-yl)-4-(2-morpholin-4-yl-ethoxy)-phenyl]-benzamide hydrate and Table 1 above shows a list of peaks of PXRD pattern of 3-methoxy-N-[3-(2-methyl-2H-pyrazol-3-yl)-4-(2-morpholin-4-yl-ethoxy)-phenyl]-benzamide hydrate collected by X'Pert HighScore software.

Differential scanning calorimetry (DSC) studies were conducted using a TA Instruments, Q2000 (EQ0090 or EQ1980) at heating rate 10° C./min from ~25° C. to ~270° C. The instruments were calibrated by the vendor for temperature and energy using the melting point and enthalpy of fusion of an indium standard. Thermal events (desolvation, melting, etc.) were evaluated using Universal Analysis 2000 software, version 4.1D, Build 4.1.0.16.

Thermogravimetric analyses (TGA) were conducted using a TA Instruments TGA Q500 (EQ0089) or Q5000 (EQ1982) at heating rate 10° C./min. The instruments were calibrated by the vendor for temperature using Alumel and Nickel standards (Curie points) and for weight using a standard weight. Thermal events such as weight-loss are calculated using the Universal Analysis 2000 software, version 4.1D, Build 4.1.0.16.

The DSC and TGA plots of 3-methoxy-N-[3-(2-methyl-2H-pyrazol-3-yl)-4-(2-morpholin-4-yl-ethoxy)-phenyl]-benzamide hydrate are shown in FIG. 2. The TGA thermogram shows that the onset of weight loss event occurred at ~41° C. at 10° C./min. The weight loss of 3.8% as shown on the TGA thermogram suggests about one mole of $H_2O$ was loss (theoretical value is 4.0%). The DSC thermogram shows a broad endotherm peak at between 50~90° C. that is consistent with the loss of $H_2O$ from dehydration. The DSC thermogram also shows an apparent recrystallization exotherm after the dehydration, and a melting endotherm with an onset of ~105° C.

Example 3

(4-(2-(4-(3-Methoxybenzamido)-2-(1-methyl-1H-pyrazol-5-yl)phenoxy)ethyl)morpholin-4-ium Carboxyformate Ethanol Solvate To a 1-liter jacketed reactor equipped with an overhead stirrer, nitrogen inlet and bottom drain valve was charged, N-(4-hydroxy-3-(1-methyl-1H-pyrazol-5-yl)phenyl-3-methoxybenzamide (35.0 g, 108 mmol), ethyl hydroxymorpholine (29.8 g, 227 mmol) and triphenylphosphine (59.6 g, 227 mmol). The reaction was cooled to −8° C. (jacket) and diisopropyl azodicarboxylate (46.0 g, 227 mmol) was added at −6 to 5° C., over 30 min. The reaction was then allowed to warm to 25° C. and stirred for approximately 3 days. The reaction was cooled again to −5° C. and ethyl hydroxymorpholine (0.1 eq.), triphenylphosphine (0.1 eq.) and diisopropyl azodicarboxylate (0.1 eq.) were added. After 25 min, the reaction was warmed to 25° C. The reaction mixture was divided in seven aliquots, approximately equal by weight. One such aliquot was concentrated, the residue was taken up in ethanol (95%) and oxalic acid (1.46 g, 0.5 eq.) was added. The mixture was stirred overnight at 20-25° C. during which time a precipitate formed. The mixture was filtered at room temperature for 1.5 h and the solid was dried to give the title compound (5.49 g).

Representative DSC and TGA plots of (4-(2-(4-(3-methoxybenzamido)-2-(1-methyl-1H-pyrazol-5-yl)phenoxy)ethyl)morpholin-4-ium carboxyformate ethanol solvate are shown in FIG. 3. The TGA thermogram of (4-(2-(4-(3-methoxybenzamido)-2-(1-methyl-1H-pyrazol-5-yl)phenoxy)ethyl)morpholin-4-ium carboxyformate ethanol solvate shows two primary weight loss events occurred prior to the degradation of the free base. The first weight loss event is consistent with the loss of approximately 0.59 moles of ethanol; the second weight loss event suggests about 0.5 moles of oxalic acid was lost.

Figure 4:
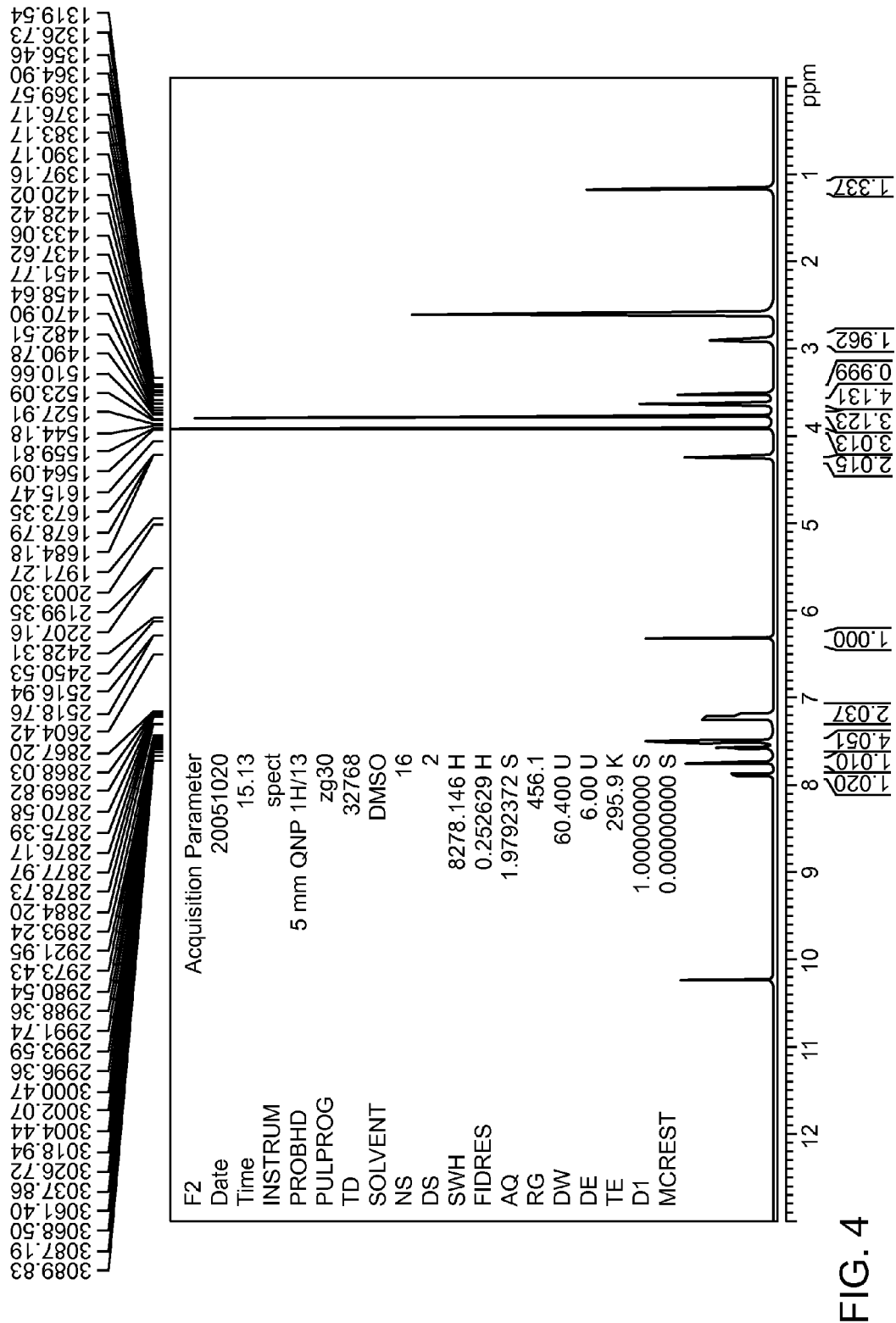
FIG. 4 shows a proton NMR of (4-(2-(4-(3-methoxybenzamido)-2-(1-methyl-1H-pyrazol-5-yl)phenoxy)ethyl)morpholin-4-ium carboxyformate ethanol solvate.

A proton NMR of (4-(2-(4-(3-methoxybenzamido)-2-(1-methyl-1H-pyrazol-5-yl)phenoxy)ethyl)morpholin-4-ium carboxyformate ethanol solvate is shown in FIG. 4.

Those skilled in the art will recognize that various modifications, additions, substitutions, and variations to the illustrative examples set forth herein can be made without departing from the spirit of the invention and are, therefore, considered within the scope of the invention.

What is claimed is:

1. 3-Methoxy-N-[3-(2-methyl-2H-pyrazol-3-yl)-4-(2-morpholin-4-yl-ethoxy)-phenyl]-benzamide hydrate with an XRPD, measured with CuKα radiation, having peaks, in terms of 2θ, chosen from those having about the following values: 5.0998, 18.7064, 19.1157, 19.3029, and 23.6567.

2. A pharmaceutical composition comprising a hydrate of claim 1 and at least one pharmaceutically acceptable carrier.

3. A method of treating a $5HT_{2A}$-related disorder comprising administering to a patient having said disorder a therapeutically effective amount of a hydrate of claim 1.

4. The method according to claim 3 wherein the $5HT_{2A}$-related disorder is selected from a condition associated with platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia, sleep disorders, diabetic-related disorders and progressive multifocal leukoencephalopathy.

5. The method according to claim 4 wherein the $5HT_{2A}$-related disorder is a condition associated with platelet aggregation.

6. A method of treating a $5HT_{2A}$-related disorder comprising administering to a patient having said disorder a therapeutically effective amount of a pharmaceutical composition of claim 2.

7. The method according to claim 6 wherein the $5HT_{2A}$-related disorder is selected from a condition associated with platelet aggregation, coronary artery disease, myocardial infarction, transient ischemic attack, angina, stroke, atrial fibrillation, blood clot formation, asthma or symptoms thereof, agitation or a symptom thereof, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia, sleep disorders, diabetic-related disorders and progressive multifocal leukoencephalopathy.

8. The method according to claim 7 wherein the $5HT_{2A}$-related disorder is a condition associated with platelet aggregation.

9. 3-Methoxy-N-[3-(2-methyl-2H-pyrazol-3-yl)-4-(2-morpholin-4-yl-ethoxy)-phenyl]-benzamide hydrate prepared by a process comprising: adding aqueous base to a solution of 4-(2-(4-(3-methoxybenzamido)-2-(1-methyl-1H-pyrazol-5-yl)phenoxy)ethyl)morpholin-4-ium chloride; and collecting the 3-methoxy-N[3-(2-methyl-2H-pyrazol-3-yl)-4-(2-morpholin-4-yl-ethoxy)-phenyl]-benzamide hydrate, wherein said 3-methoxy-N-[3-(2-methyl-2H-pyrazol-3-yl)-4-(2-morpholin-4-yl- has an XRPD, measured with CuKα radiation, having peaks, in terms of 2θ, chosen from those having about the following values: 5.0998, 18.7064, 19.1157, 19.3029, and 23.6567.

10. A solid pharmaceutical composition comprising 3-methoxy-N-[3-(2-methyl-2H-pyrazol-3-yl)-4-(2-morpholin-4-yl-ethoxy)-phenyl]-benzamide hydrate prepared by a process comprising: formulating a therapeutically effective amount of 3-methoxy-N-[3-(2-methyl-2H-pyrazol-3-yl)-4-(2-morpholin-4-yl-ethoxy)-phenyl]-benzamide hydrate and at least one pharmaceutically acceptable carrier to produce a solid pharmaceutical composition, wherein said 3-methoxy-N-[3-(2-methyl-2H-pyrazol-3-yl)-4-(2-morpholin-4-yl- has an XRPD, measured with CuKα radiation, having peaks, in terms of 2θ, chosen from those having about the following values: 5.0998, 18.7064, 19.1157, 19.3029, and 23.6567.

11. The solid pharmaceutical composition according to claim 10, wherein the pharmaceutical composition is in a form chosen from powders, tablets, pills, capsules, cachets, suppositories, dispersible granules, and lozenges.

12. The method according to claim 5, wherein the condition associated with platelet aggregation is chosen from claudication, peripheral artery disease, vasoconstriction, vasospasm, thrombosis, and stroke.

13. The method according to claim 8, wherein the condition associated with platelet aggregation is chosen from claudication, peripheral artery disease, vasoconstriction, vasospasm, thrombosis, and stroke.

* * * * *